United States Patent
Duan

(10) Patent No.: US 9,840,712 B2
(45) Date of Patent: Dec. 12, 2017

(54) CD133 APTAMERS FOR DETECTION OF CANCER STEM CELLS

(71) Applicant: DEAKIN UNIVERSITY, Victoria (AU)

(72) Inventor: Wei Duan, Victoria (AU)

(73) Assignee: DEAKIN UNIVERSITY, Waurn Ponds, Victoria (AU)

( * ) Notice: Subject to any disclaimer, the term of this patent is extended or adjusted under 35 U.S.C. 154(b) by 0 days.

(21) Appl. No.: 14/418,648

(22) PCT Filed: Aug. 2, 2013

(86) PCT No.: PCT/AU2013/000850
§ 371 (c)(1),
(2) Date: Jan. 30, 2015

(87) PCT Pub. No.: WO2014/019024
PCT Pub. Date: Feb. 6, 2014

(65) Prior Publication Data
US 2015/0299708 A1  Oct. 22, 2015

(30) Foreign Application Priority Data

Aug. 2, 2012 (AU) .................................. 2012903332

(51) Int. Cl.
| C12N 15/11 | (2006.01) |
| A61K 31/7105 | (2006.01) |
| A61K 48/00 | (2006.01) |
| C12N 15/115 | (2010.01) |
| G01N 33/68 | (2006.01) |

(52) U.S. Cl.
CPC ....... *C12N 15/115* (2013.01); *G01N 33/6872* (2013.01); *C12N 2310/16* (2013.01); *C12N 2310/334* (2013.01); *C12N 2310/335* (2013.01); *C12N 2310/3517* (2013.01); *C12N 2320/30* (2013.01); *G01N 2333/70596* (2013.01)

(58) Field of Classification Search
None
See application file for complete search history.

(56) References Cited

U.S. PATENT DOCUMENTS

| 5,270,163 | A | 12/1993 | Gold et al. |
| 5,475,096 | A | 12/1995 | Gold et al. |
| 5,637,459 | A * | 6/1997 | Burke .............. A61K 47/48076 435/5 |
| 2007/0050146 | A1* | 3/2007 | Bentwich .............. C12N 15/111 702/19 |
| 2009/0047295 | A1* | 2/2009 | Berry ...................... A61K 31/00 424/174.1 |
| 2011/0206614 | A1 | 8/2011 | McAllister et al. |

FOREIGN PATENT DOCUMENTS

| JP | 2007-319153 A | 12/2007 |
| WO | 00/56930 | 9/2000 |
| WO | 2003/066097 A2 | 8/2003 |
| WO | 2004/084950 A2 | 10/2004 |
| WO | 2006/051405 A2 | 5/2006 |

OTHER PUBLICATIONS

Karaballi et al (Phys.Chem.Chem.Phys.,2015, 17, 21356).*
Australian Patent Office, International Search Report for International Application No. PCT/AU2013/000850 dated Sep. 26, 2013, 33 pages.
Australian Patent Office, Written Opinion for International Application No. PCT/AU2013/000850 dated Sep. 26, 2013, 6 pages.
Cerchia, Laura et al., Nucleic acid aptamers in cancer medicine, FEBS Letters 528, 2002, 12-16.
Kanwar, Jagat R. et al., "Chimeric aptamers in cancer cell-targeted drug delivery", Critical Reviews in Biochemistry and Molecular Biology, 46(6), 2011, 459-477.
Shigdar, Sarah et al., "RNA aptamers targeting cancer stem cell marker CD133", Cancer Letters 330, 2013, 84-95.
Yin, A.H. et al., "AC133, a Novel Marker for Human Hematopoietic Stem and Progenitor Cells," Blood, 90, 1997, 5002-5012.
European Patent Office, "Extended European Search Report dated Mar. 7, 2016", European Patent Application No. 13825421.4, Mar. 7, 2016, 11 Pages.
Ferrandina, et al., "Targeting CD133 Antigen in Cancer", Expert Opin. Ther. Targets 13(7):823-837 (http://dx.doi.org/10.1517/14728220903005616), Jun. 17, 2009, 16 Pages.
Ray et al., Aptamers for Targeted Drug Delivery, Pharmaceuticals 2010; 3: 1761-1778.
Further Examination Report dated Sep. 15, 2017, issued by the New Zealand Intellectual Property Office, IP Number: 704719, Patent: DC 133 Aptamers for Detection of Cancer Stem Cells, pp. 1-5.

* cited by examiner

*Primary Examiner* — Richard Schnizer
(74) *Attorney, Agent, or Firm* — Dorsey & Whitney LLP

(57) ABSTRACT

The present disclosure relates to RNA aptamers and uses thereof, in particular, aptamers which specifically bind to CD133 and which demonstrate superior tumor penetration.

19 Claims, 7 Drawing Sheets

1. A 15-mer CD133 RNA aptamer (CD133-1-2-2)
5'-CCCUCCUACAUAGGG-3'

2. A 19-mer CD133 RNA aptamer (CD133-2-1)
5'-CAGAACGUAUACUAUUCUG-3'

FIGURE 1

SEQUENCE LISTING

```
<160> NUMBER OF SEQ ID NOS: 8

<210> SEQ ID NO 1
<211> LENGTH: 15
<212> TYPE: RNA
<213> ORGANISM: Artificial Sequence
<220> FEATURE:
<223> OTHER INFORMATION: chemically synthesized

<400> SEQUENCE: 1
cccuccuaca uaggg                                                       15

<210> SEQ ID NO 2
<211> LENGTH: 81
<212> TYPE: RNA
<213> ORGANISM: Artificial Sequence
<220> FEATURE:
<223> OTHER INFORMATION: chemically synthesized

<400> SEQUENCE: 2
gagacaagaa uaaacgcuca acccacccuc cuacauaggg aggaacgagu uacuauagag      60
cuucgacagg aggcucacaa c                                                81
```

-continued

```
<210> SEQ ID NO 3
<211> LENGTH: 58
<212> TYPE: RNA
<213> ORGANISM: Artificial Sequence
<220> FEATURE:
<223> OTHER INFORMATION: chemically synthesized

<400> SEQUENCE: 3
gagacaagaa uaaacgcuca acccacccuc cuacauaggg aggaacgagu uacuauag        58

<210> SEQ ID NO 4
<211> LENGTH: 35
<212> TYPE: RNA
<213> ORGANISM: Artificial Sequence
<220> FEATURE:
<223> OTHER INFORMATION: chemically synthesized

<400> SEQUENCE: 4
gcucaaccca cccuccuaca uagggaggaa cgagu                                 35

<210> SEQ ID NO 5
<211> LENGTH: 21
<212> TYPE: RNA
<213> ORGANISM: Artificial Sequence
<220> FEATURE:
<223> OTHER INFORMATION: chemically synthesized

<400> SEQUENCE: 5
ccacccuccu acauagggug g                                                21

<210> SEQ ID NO 6
<211> LENGTH: 19
<212> TYPE: RNA
<213> ORGANISM: Artificial Sequence
<220> FEATURE:
<223> OTHER INFORMATION: chemically synthesized

<400> SEQUENCE: 6
cagaacguau acuauucug                                                   19

<210> SEQ ID NO 7
<211> LENGTH: 15
<212> TYPE: RNA
<213> ORGANISM: Artificial Sequence
<220> FEATURE:
<223> OTHER INFORMATION: chemically synthesized

<400> SEQUENCE: 7
agaacguaua cuauu                                                       15

<210> SEQ ID NO 8
<211> LENGTH: 85
<212> TYPE: RNA
<213> ORGANISM: Artificial Sequence
<220> FEATURE:
<223> OTHER INFORMATION: hemically synthesized

<400> SEQUENCE: 8
gagacaagaa uaaacgcuca aggaaagcgc uuauuguuug cuauguuaga acguauacua       60
uuucgacagg aggcucacaa caggc                                            85
```

CD133 APTAMERS FOR DETECTION OF CANCER STEM CELLS

CROSS-REFERENCE TO RELATED APPLICATIONS

The present application is a Section 371 National Stage Application of International Application No. PCT/AU2013/000850, filed on Aug. 2, 2013, which claims priority to Australian Application No. 2012903332, filed on Aug. 2, 2012, both of which are hereby incorporated by reference in their entirety.

SEQUENCE LISTING

A sequence listing submitted in computer readable format is hereby incorporated by reference. The computer readable file is named P516251WOUS01_ST25.txt and contains 4.00 kilobytes.

RELATED APPLICATIONS AND INCORPORATION BY REFERENCE

All documents cited or referenced herein, and all documents cited or referenced in herein cited documents, together with any manufacturer's instructions, descriptions, product specifications, and product sheets for any products mentioned herein or in any document incorporated by reference herein, are hereby incorporated herein by reference in their entirety.

FIELD OF THE INVENTION

The present disclosure relates to RNA aptamers and uses thereof, in particular, aptamers which specifically bind to CD133 and which demonstrate superior tumour penetration.

BACKGROUND OF THE INVENTION

CD133, also known as Prominin-1 is a pentaspan, highly glycosylated, membrane glycoprotein that is associated with cholesterol in the plasma membrane. Though this protein is known to define a broad population of cells, including somatic stem and progenitor cells, and is expressed in various developing epithelial and differentiated cells, its exact function is still being elucidated. It has however been linked to the Notch-signalling pathway which is critical for binary cell fate, differentiation of intestinal epithelium, and lymphopoiesis (Ulasov et al. 2011. Mol Med 17:103-12). More interest has been shown in this molecule in recent years due to it being thought to be a marker of cancer stem cells (CSCs) in a number of cancers. Indeed, growing evidence has shown that CD133 is expressed on CSCs in a number of cancers, and there is an enhanced tumorigenic potential of CD133$^+$ cells versus their negative counterparts in immunodeficient mice (Dittfeld et al. 2009. Radiother Oncol 92:353-61).

Immunotherapy has had a great impact on the treatment of cancer in recent years. However, the use of antibodies, even humanised antibodies, can lead to adverse side effects that can be fatal (Hansel et al. 2010. Nat Rev Drug Discov 9:325-38). This has led to the search for 'bigger and better' options. There have been several attempts made to use nucleic acids as therapeutics though these have met with disappointing results, not least because of the failure of these nucleic acids to enter the cell (Shigdar et al. 2011. Br J Haematol 155:3-13).

Chemical antibodies, termed aptamers, have been increasingly utilised for clinical applications in the last twenty years. Indeed, one aptamer, pegaptanib (an anti-VEGF aptamer) has been approved by the FDA and several more are in clinical trials. Increased interest in the use of aptamers for therapy is due to several reasons, including the fact that they exhibit no immunogenicity, little batch-to-batch variation due to being chemically synthesized, and are more stable than conventional antibodies. Due to their small size, they also show superior tumour penetration. However, their most important feature is the ability to attach these aptamers to nanoparticles, drugs, imaging agents or other nucleic acid therapeutics without loss-of-function (Meng et al. 2012. PLoS One 7:e33434). This functionalisation is leading to new and more targeted therapies, with fewer side effects than current treatment modalities (Meng et al. 2012 supra). When compared to conventional treatment which is largely a passive process, targeted delivery systems are much more effective. For an aptamer to be an effective drug delivery agent, the aptamer must bind to its target on the cell surface and be internalised within a short period of time.

SUMMARY OF THE INVENTION

It has recently been appreciated that cancer stem cells are responsible for the formation and growth of neoplastic tissue and are naturally resistant to chemotherapy, explaining why traditional chemotherapies can initially shrink a tumour but fail to eradicate it in full, resulting in eventual recurrence. According to the cancer stem cell hypothesis, CD133-positive cells determine long-term tumour growth and, therefore are suspected to influence clinical outcome. It has been recently found that both the proportion of CD133-positive cells and their topological organisation in clusters were significant prognostic factors for adverse progression-free survival and overall survival independent of tumour grade, extent of resection, or patient age.

Current histopathological techniques for detection and targeting of CD133-positive cancer stem cells use conventional antibody-based systems, but lack sensitivity due to the size of the anti-CD133 antibodies available and their relative inability to penetrate tissues.

Accordingly, the generation of aptamers to CD133$^+$ cells would be advantageous in the eradication of cancer. This has been addressed by the present inventor who has generated aptamers specific for CD133 which are rapidly internalised and show superior tumour penetration.

The present disclosure provides an isolated RNA aptamer which specifically binds to CD133. In one example, the CD133 is human CD133.

In one example, the aptamers of the present disclosure have a dissociation constant for CD133 expressed on HT-29 cells in the range of from 82-145 nM. In another example, the aptamers of the present disclosure have a dissociation constant for CD133 expressed on Hep3B cells in the range of from 32-52 nM.

In one example, the isolated RNA aptamer comprises a consensus sequence 5'-CCCUCCUACAUAGGG-3' (SEQ ID NO:1).

In another example, the isolated RNA aptamer comprises a sequence selected from the following:
(i) 5'-GAG ACA AGA AUA AAC GCU CAA CCC A CCCUCCUACAUAGGGAG GAA CGA GUU ACU AUA GAG CUU CGA CAG GAG GCU CAC AAC-3' (SEQ ID NO:2);

(ii) 5'-GAG ACA AGA AUA AAC GCU CAA CCC A<u>CCCUCCUACAUAGGG</u>AG GAA CGA GUU ACU AUA G-3' (SEQ ID NO:3);

(iii) 5'-GCU CAA CCC A<u>CCCUCCUACAUAGGG</u>AG GAA CGA GU-3' (SEQ ID NO:4);

(iv) 5'-CC A<u>CCCUCCUACAUAGGG</u>UG G-3' (SEQ ID NO:5); and (v) 5'-<u>CCCUCCUACAUAGGG</u>-3' (SEQ ID NO:1).

In another example, the isolated RNA aptamer comprises a consensus sequence 5'-CAGAACGUAUACUAUUCUG-3' (SEQ ID NO:6).

In another example, the isolated RNA aptamer comprises a consensus sequence 5'-AGAACGUAUACUAUU-3' (SEQ ID NO:7).

In another example, the isolated RNA aptamer comprises the sequence 5'-GAG ACA AGA AUA AAC GCU CAA GGA AAG CGC UUA UUG UUU GCU AUG UU <u>AGAACGUAUACUAUU</u> CGA CAG GAG GCU CAC AAC AGG C-3' (SEQ ID NO:8).

In a particular example, the present disclosure provides an isolated RNA aptamer which is 2'-fluoro-pyrimidine modified and which specifically binds to CD133.

In another example, the isolated RNA aptamer consists essentially of the sequence of SEQ ID NO:1 or SEQ ID NO:6.

In another example, the isolated RNA aptamer consists of the sequence of SEQ ID NO:1 or SEQ ID NO:6.

In another example, the isolated RNA aptamer comprises a consensus sequence CCCUCCUACAUAGGG (SEQ ID NO:1), or a consensus sequence CAGAACGUAUACUAUUCUG (SEQ ID NO:6), or a consensus sequence AGAACGUAUACUAUU (SEQ ID NO:7), wherein the sequence length is between 15 bases and 100 bases. In another example, the length is between 15 and 40 bases. In another example, the sequence length is between 19 bases and 100 bases. In a further example, the length is between 19 and 40 bases.

The sequence may comprise one or more base substitutions within the consensus sequence which maintain the binding loop of the aptamer. In one example the sequence comprises one or more substitutions within the consensus sequence. In one example, the sequence comprises at least one, two, three, four, five or six substitutions within the consensus sequence. In another example, the sequence comprises at least one, two, three, four, five or six substitutions within the stem region of the aptamer according to SEQ ID NO:1 or SEQ ID NO:6. In one example, the stem region is that of the predicted two dimensional structure of the aptamer.

In one example, the aptamer comprises one or more modifications (modified aptamer) that improve aptamer stability (in vitro or in vivo). Suitable modifications are discussed elsewhere herein. In one example, the pyrimidine bases are 2'-fluoro (2'-F) modified. In another example, the 3' end of the RNA aptamer is modified to protect it from nuclease digestion. In another example, aptamer is modified by coupling the 5' end to a fluorophore or inverted dT.

The present disclosure also provides an isolated RNA aptamer having substantially the same ability to bind to CD133 as that of an aptamer comprising a sequence of SEQ ID NO:1 or SEQ ID NO:6, or SEQ ID NO:7.

In one example, the aptamer specifically binds to CD133$^+$ cell(s). In another example, the CD133+ cell(s) is a stem cell(s). In another example, the stem cell is an isolated cancer stem cell(s). In another example, the cancer stem cell(s) is characterised as (i) expressing CD133, (ii) is tumorigenic, (iii) is capable of self renewal (iv) is capable of differentiating and (v) resistant to apoptosis by conventional therapy.

The cancer stem cells may be alternatively described as isolated, enriched or purified from a source, such as a biological sample. In another example, the cancer stem cell(s) represent a population of cells enriched on the basis of CD133$^+$ expression. In another example, the population of cells comprises at least 30%, 40%, 50%, 60%, 70%, 80%, 90% or 95% cancer stem cells.

In one example, the CD133 expressing cells and/or cancer stem cells are present in vivo. In another example, the CD133 expressing cells and/or cancer stem cells are present in vitro. In a further example, the C133 expressing cells and/or cancer stem cells are present in a biological sample obtained from a subject.

In another example, the CD133 expressing cells and/or cancer stem cells of the present disclosure may express one or more additional antigens including CD44, ABCG2, β-catenin, CD117, ALDH, VLA-2, CD166, CD201, IGFR, EpCAM, and EGF1R.

In another example, the cancer stem cell according to the present disclosure is a brain cancer stem cell, a breast cancer stem cell, a prostate cancer stem cell, a pancreatic cancer stem cell, a colon cancer stem cell, a liver cancer stem cell, a lung cancer stem cell, an ovarian cancer stem cell, a skin cancer stem cell or a melanoma stem cell.

The present disclosure also provides a diagnostic agent comprising an RNA aptamer as described herein.

In one example, the diagnostic agent comprises an RNA aptamer of the present disclosure coupled to a detectable label.

It would be appreciated by persons skilled in the art that the aptamers of the present invention avoid complications that may be associated with non-specific antibody binding and hence provide superior signal to noise ratio.

In one example, the diagnostic agent as described herein is used to detect for CD133 expressing cancer stem cells in vivo or in vitro.

In one example, the RNA aptamer of the present disclosure can be used diagnostically to detect the presence of CD133 expressing cells and/or cancer stem cells in a subject or in a biological sample obtained from a subject having a tumour or suspected of having a tumour. Detection can be facilitated by coupling the aptamer to a detectable label. Examples of detectable labels include various enzymes, prosthetic groups, fluorescent materials, luminescent materials, bioluminescent materials, electron dense labels, labels for MRI and radioactive materials.

The present disclosure also provides an RNA aptamer as described herein or the diagnostic agent as described herein for use in histological examination of biological samples. Methods for preparing histological preparations will be familiar to persons skilled in the art.

The present disclosure also provides an anticancer agent comprising an RNA aptamer as described herein.

In one example, the anticancer agent comprises an RNA aptamer of the present disclosure coupled to a moiety.

In one example, the anticancer agent as described herein is used to treat a cancer in a subject. In one example, the subject is one which would benefit from treatment with the RNA aptamer of the present disclosure. In another example, the subject is one which has been diagnosed as having cancer. In a further example, the subject is one which has a cancer selected from brain cancer, breast cancer, prostate cancer, pancreatic cancer, colon cancer, liver cancer, lung cancer, ovarian cancer, skin cancer, melanoma or any other cancer in which CD133+ cells are present.

The aptamer of the present disclosure can be coupled to a moiety and the aptamer used to direct the moiety to the site of a tumour which comprises, or is suspected of comprising a CD133 expressing cancer stem cell(s). Examples of moieties include toxins, radionuclides or chemotherapeutic agents which can be used to kill cancer stem cells, or imaging agents which can be used to locate and size tumours comprising CD133 expressing cells.

The anticancer agent comprising the RNA aptamer of the present disclosure can additionally include one or more effective ingredients.

The present disclosure also provides a method for isolating, purifying or enriching a CD133 expressing cell(s) and/or cancer stem cell(s) from a biological sample obtained from a subject, the method comprising contacting the cell with an RNA aptamer of the present disclosure or the diagnostic agent of the present disclosure. In one example, the method is carried out in vitro.

Methods isolating, purifying or enriching CD133 expressing cells are known to persons skilled in the art and are also described elsewhere herein.

The present disclosure also provides a method for identifying a CD133 expressing cell(s) and/or cancer stem cell(s) in a subject or in a biological sample obtained from a subject having, or suspected of having cancer, the method comprising contacting the cell with an isolated RNA aptamer of the present disclosure or the diagnostic agent of the present disclosure.

The present disclosure also provides a method for treating or preventing cancer in a subject comprising providing a subject with an RNA aptamer as described herein or the anticancer agent as described herein.

In one example, the cancer is any cancer in which CD133 expressing cells and/or cancer stem cells are present or suspected of being present. In another example, the subject is one which has been diagnosed as having cancer. In a further example, the subject is one which has a cancer selected from brain cancer, breast cancer, prostate cancer, pancreatic cancer, colon cancer, liver cancer, lung cancer, ovarian cancer, skin cancer, melanoma or any other cancer in which CD133+ cells are present.

The present disclosure also relates to the use of an RNA aptamer or anticancer agent as described herein in medicine.

The present disclosure also relates to the use of an RNA aptamer or anticancer agent as described herein for treating or preventing cancer in a subject.

The present disclosure also relates to the use of an RNA aptamer or anticancer agent as described herein in the manufacture of a medicament for treating or preventing cancer in a subject.

The present invention also relates to a delivery agent comprising an RNA aptamer as described herein coupled to an siRNA or ribozyme.

The present disclosure also provides a composition comprising a therapeutically effective amount of an RNA aptamer, anticancer agent or delivery agent as described herein, together with a pharmaceutically acceptable carrier and/or excipient.

The present disclosure also provides an RNA aptamer as described herein or the diagnostic agent as described herein for use in molecular imaging of tumours.

The tumour penetrative ability of the RNA aptamers of the present invention provide a distinct advantage over antibodies for molecular imaging of tumors. For example, the RNA aptamers can be coupled to an agent which facilitates the detecting and imaging of tumours bearing CD133 expressing cells. Examples of suitable agents include the detection labels are described herein.

The RNA aptamer, diagnostic agent, anticancer agent, delivery agent or pharmaceutical composition as described herein may be used alone or in combination with other treatment modalities. For example, the RNA aptamer, diagnostic agent, anticancer agent, delivery agent or pharmaceutical composition may be used in combination with chemotherapy and/or radiotherapy. While not wishing to be bound by theory, it is postulated that the chemotherapy or radiotherapeutic agents can be used to shrink tumours by primarily targeting rapidly dividing cells which are typically the progeny cells of the cancer stem cells. The diagnostic agent can be used to determine the effectiveness of any prior treatment modality to eliminate cancer stem cells by detecting the presence or absence of cancer stem cells in the tumour. The anticancer agent, delivery agent or pharmaceutical composition containing the RNA aptamer of the present disclosure can then be administered to the site of the tumour to specifically deplete cancer stem cells. Accordingly, the anticancer agent, delivery agent or pharmaceutical composition containing the RNA aptamer can be used together with chemotherapy or radiotherapy or subsequent to chemotherapy or radiotherapy treatment. It is also contemplated that the RNA aptamer of the present disclosure can be combined with one or more additional aptamers which target an antigen present on a cancer stem cell.

Each example of the disclosure shall be taken to apply mutatis mutandis to a method for treating, preventing or ameliorating cancer in a subject.

Each example of the disclosure shall be taken to apply mutatis mutandis to molecular imaging of tumours.

BRIEF DESCRIPTION OF THE DRAWINGS

FIG. 1. Sequence of RNA aptamers; a 15 mer CD133 RNA aptamer designated CD133-1-2-2 (SEQ ID NO:1) and a 19 mer CD133 RNA aptamer designated CD133-2-1 (SEQ ID NO:6).

Base modification, 2'-F-Pyrimidine RNA, cytidine (C), and uridine (U) are 2'-F modified (see underlining in Figure). IDT-3' to protect it from nuclease digestion. RNA HPLC grade purification, Post Synthesis: 2'-Deprotect/Desalt.

Figure 2:
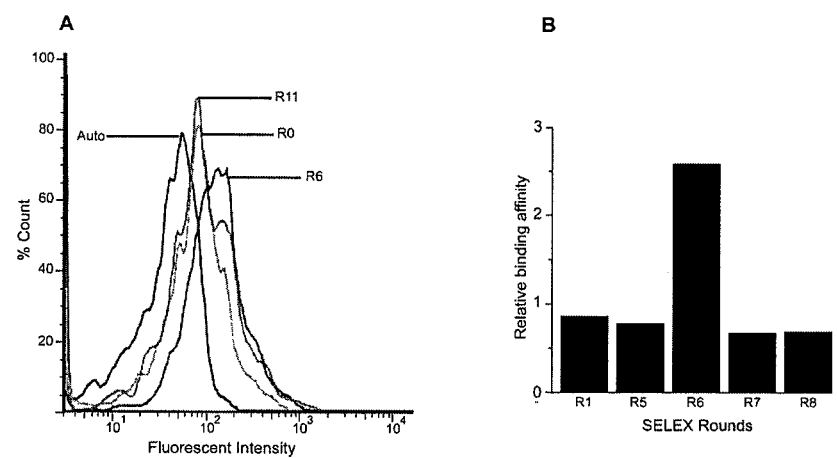

FIG. 2. Isolation of CD133 aptamers using systematic evolution of ligands by exponential enrichment (SELEX).

(A) Flow cytometric binding analysis of FITC-labelled aptamers from iterative rounds of SELEX to CD133-transfected HEK293T cells. Fluorescein-labelled RNA from each round was incubated with target cells at 37° C. for 30 minutes, followed by flow cytometric analysis. (B) The binding of each round was calculated after subtracting the mean fluorescent intensity of the binding of unselected library RNA to target cells, as well as that for binding to negative control cells. R, round in SELEX cycle; R, unselected random library.

Figure 3:
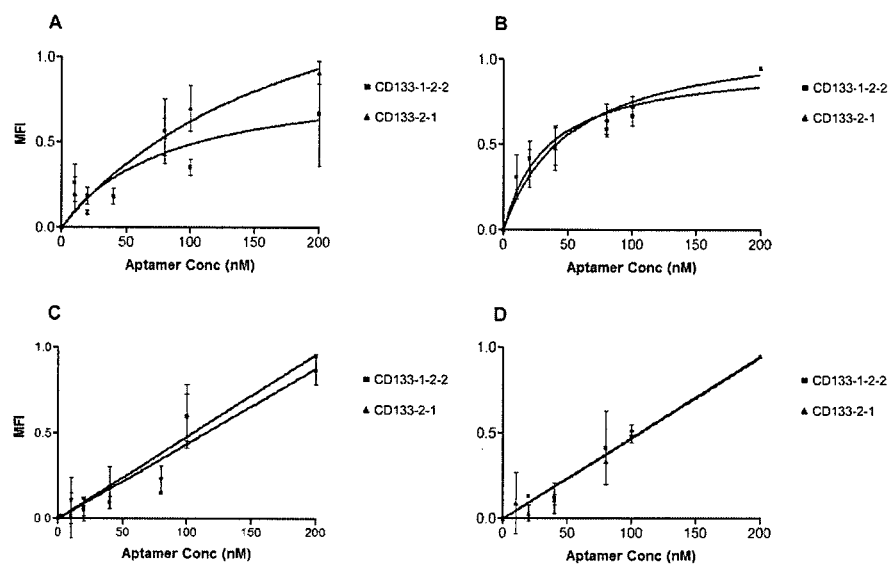

FIG. 3. Determination of equilibrium dissociation constants ($K_D$) for the interaction of truncated clones of CD133 aptamers.

Representative binding curves at varying concentrations of CD133 aptamers (1-200 nM) at a cell density of $5\times10^5$ cells/mL. (A) HT-29 cells; (B) Hep3B cells; (C) T98G cells; (D) HEK293T cells.

Figure 4:
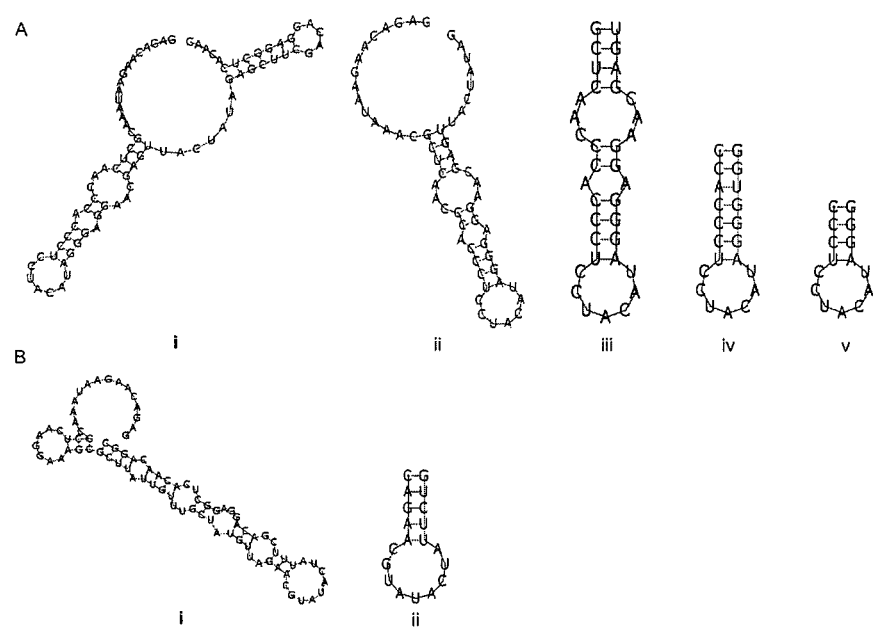

FIG. 4 Truncation of CD133 aptamers.

(A) CD133-1 was serially truncated a total of 4 times (i): CD133-1; (ii): CD133-1-1, (iii): CD133-1-2, (iv): CD133-1-2-1, (v): CD133-1-2-2); (B) (i) CD133-2 was truncated once (ii) CD133-2-1.

Figure 5:
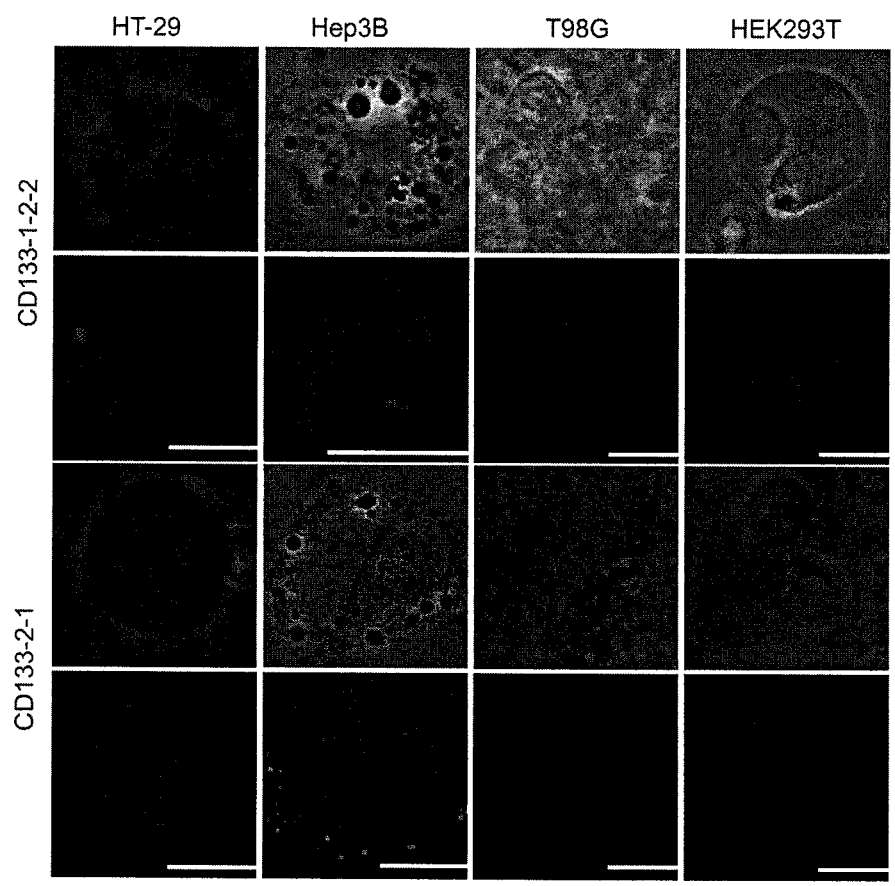

FIG. 5. CD133 aptamers are endocytosed following binding to CD133-positive cells but not to CD133-negative cells.

DY647-labelled CD133 aptamers were incubated with indicated cancer cells for 30 min at 37° C., followed by imaging using laser scanning confocal microscopy. For each pair of panels, optical (phase) images are on the top, and fluorescent images are on the bottom. HT-29 and Hep3B are human colon and liver cancer cells, respectively that express CD133. T98G is human glioma cells that does not expression CD133. HEK293T is a human non-tumour cell line that does not express CD133. Scale line—20 µm.

Figure 6:
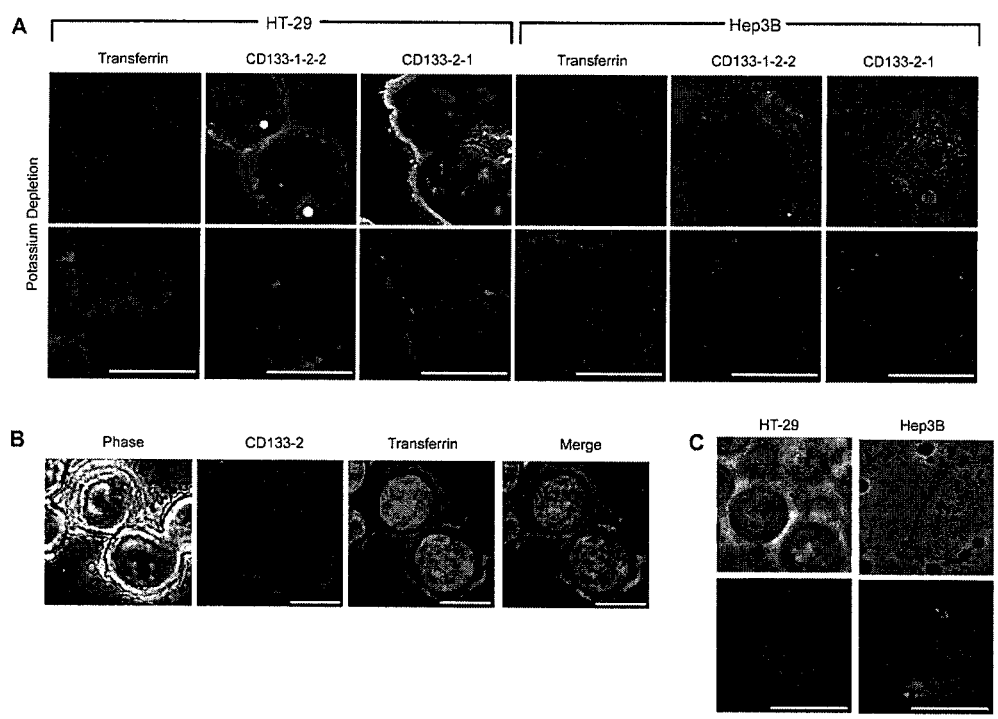

FIG. 6. CD133 aptamers are endocytosed following binding to CD133-positive cells but not to CD133-negative cells.

After treatment (potassium depletion) that arrest endocytosis, the aptamers no longer enter the cells, instead they stay on the cell surface (forming a ring structure rather than the particulate pattern). Transferrin is used as a positive control to show the effectiveness of the treatment to stop transferrin endocytosis. HT-29: colon cancer cell lines, Hep3B: human liver cancer cell line. DY647-labelled CD133 aptamers were incubated with indicated cancer cells for 30 min at 37° C., followed by imaging using laser scanning confocal microscopy. For each pair of panels, optical (phase) images are on the top, and fluorescent images are on the bottom. Scale line—20 µm.

Figure 7:
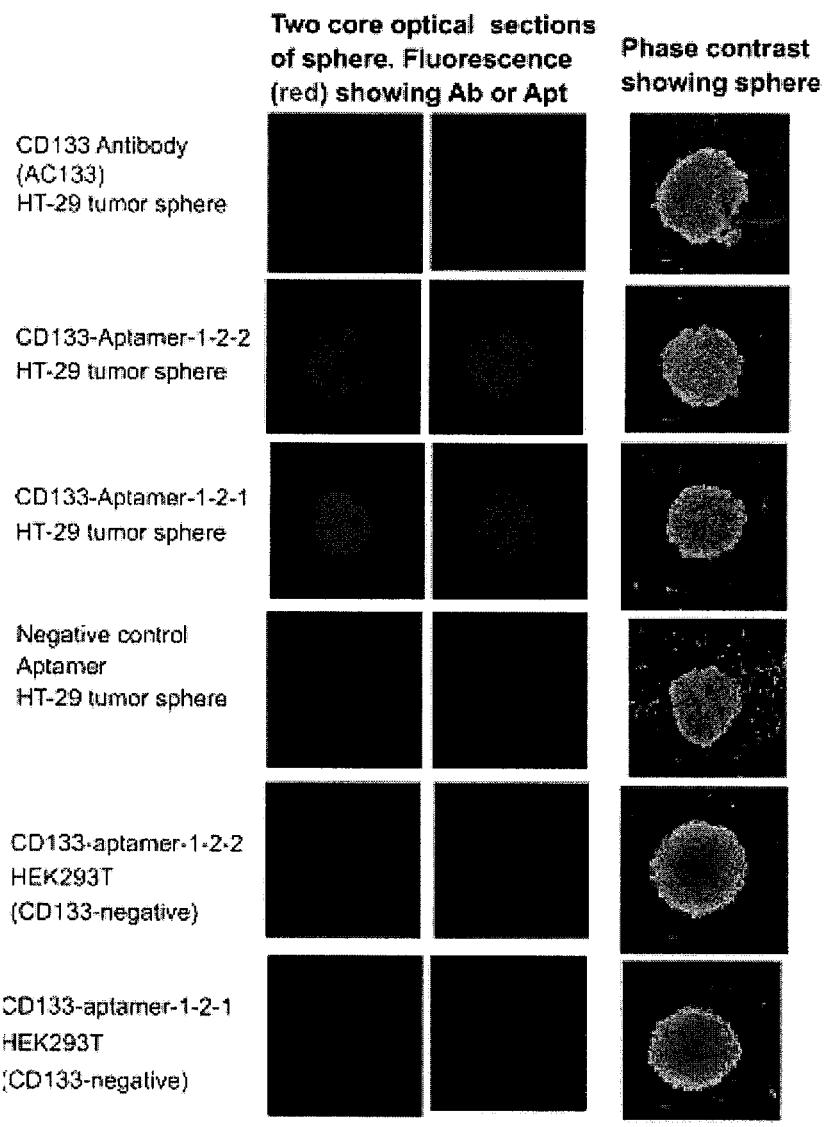

FIG. 7 CD133 RNA aptamers penetrate tumor mass much better than CD133 antibody (AC133).

CD133$^+$ human colon cancer cell (HT-29) and CD133$^-$ human kidney epithelial cells (HEK293T) cells were cultured in serum-free DMEM/F12 medium supplemented with fibroblast growth factor (10 ng/ml) and epidermal growth factor (10 ng/ml), insulin (50 µg/ml) and B27 (100 units/ml), to allow the formation of tumorsphere. When the spheres reached a size of 300 µm, the spheres were incubated with 100 nM Dy647-labelled CD133 RNA aptamers or control aptamer as well as equivalent concentration of PE-CD133 antibodies (AC133) separately for 4 hr. After washing with PBS for 3 times, the spheres were imaged using confocal fluorescence microscopy. The two core (middle) sections were shown.

KEY TO SEQUENCE LISTING

SEQ ID NO:1: is the sequence for the CD133-2-2 aptamer (15 mer)
SEQ ID NO:2: is the sequence for the CD133-1 aptamer (81 mer)
SEQ ID NO:3: is the sequence for the CD133-1-1 aptamer (58 mer)
SEQ ID NO:4: is the sequence for the CD133-1-2 aptamer (35 mer)
SEQ ID NO:5: is the sequence for the CD133-1-2-1 aptamer (21 mer)
SEQ ID NO:6: is the sequence for the CD133-2-1 aptamer (19 mer)
SEQ ID NO:7: is a consensus CD133 aptamer sequence (15 mer)
SEQ ID NO:8: is the sequence for CD133-2 aptamer (85 mer)
SEQ ID NO:9: is the sequence of the EpDT3 aptamer
SEQ ID NO:10: is the sequence of an EpCAM aptamer
SEQ ID NO:11: is a DNA library sequence with central 40 nt randomised sequence
SEQ ID NO:12: is a primer sequence
SEQ ID NO:13: is a primer sequence
SEQ ID NO:14: is sense oligonucleotide
SEQ ID NO:15: is an antisense oligonucleotide
SEQ ID NO:16: is a sense oligonucleotide
SEQ ID No:17: is an antisense oligonucleotide
SEQ ID NO:18: is a sense oligonucleotide
SEQ ID NO:19: is an antisense oligonucleotide
SEQ ID NO:20 is a sense oligonucleotide
SEQ ID NO:21: is an antisense oligonucleotide
SEQ ID NO:22: is a sense oligonucleotide
SEQ ID NO:23: is an antisense oligonucleotide
SEQ ID NO:24 is a sense oligonucleotide
SEQ ID NO:25 is an antisense oligonucleotide

DETAILED DESCRIPTION OF THE INVENTION

General Techniques and Selected Definitions

The term "and/or", e.g., "X and/or Y" shall be understood to mean either "X and Y" or "X or Y" and shall be taken to provide explicit support for both meanings or for either meaning.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each example described herein is to be applied mutatis mutandis to each and every other example of the disclosure unless specifically stated otherwise.

Those skilled in the art will appreciate that the disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure.

The present disclosure is performed without undue experimentation using, unless otherwise indicated, conventional techniques of molecular biology, recombinant DNA technology, cell biology and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, ppl-22; Atkinson et al, pp 35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series, Sakakibara, D., Teichman, J., Lien, E. Land Fenichel, R. L. (1976). *Biochem. Biophys. Res. Commun.* 73 336-342; Merrifield, R. B. (1963). *J. Am. Chem. Soc.* 85, 2149-2154; Barany, G. and Merrifield, R. B. (1979) in The Peptides (Gross, E. and Meienhofer, J. eds.), vol. 2, pp. 1-284, Academic Press, New York. 12. Wünsch, E., ed. (1974) Synthese von Peptiden in Houben-Weyls Metoden der Organischen Chemie (Müler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) *Int. J. Peptide Protein Res.* 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000), ISBN 0199637970, whole of text.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

The term "consists of" or "consisting of" shall be understood to mean that a method, process or composition of matter has the recited steps and/or components and no additional steps or components.

The term "about", as used herein when referring to a measurable value such as an amount of weight, time, dose, etc. is meant to encompass variations of ±20% or ±10%, more preferably ±5%, even more preferably ±1%, and still more preferably ±0.1% from the specified amount, as such variations are appropriate to perform the disclosed method.

The term "aptamer" as used herein refer in general to either an oligonucleotide of a single defined sequence or a mixture of said oligonucleotides, wherein the mixture retains the properties of binding specifically to CD133. As used herein, "aptamer" refers to single stranded nucleic acid. Structurally, the aptamers of the present disclosure are specifically binding oligonucleotides.

The term "oligonucleotide" as used herein is generic to polydeoxyribonucleotides (containing 2'-deoxy-D-ribose or modified forms thereof), i.e. DNA, to polyribonucleotides (containing D ribose or modified forms thereof), i.e. RNA, and to any other type of polynucleotide which is an N-glycoside or C-glycoside of a purine or pyrimidine base, or modified purine or pyrimidine base or abasic nucleotides. According to the present disclosure the term "oligonucleotide" includes not only those with conventional bases, sugar residues and internucleotide linkages, but also those that contain modifications of any or all of these three moieties.

The term "RNA aptamer" as used herein is an aptamer comprising ribonucleoside units. RNA aptamer is also meant to encompass RNA analogs as defined herein.

As used herein the term "binding affinity" and binding activity" are intended to refer to the tendency of a ligand molecule/aptamer to bind or not bind a target and describes the measure of the strength of the binding or affinity of the ligand molecule/aptamer to bind the target. The energetics of said interactions are significant in "binding activity" and "binding affinity" because they define the necessary concentrations of interacting partners, the rates at which these partners are capable of associating, and the relative concentrations of bound and free molecules in a solution. The energetics are characterized herein through, among other ways, the determination of a dissociation constant, $K_d$. As is known in the art, a low dissociation constant indicates stronger binding and affinity of the molecules to each other. In one example, the dissociation constant is at least $10^{-6}$ M. In another example, the dissociation constant is at least $10^{-8}$ and $10^{-9}$ M.

As used herein, the term "biological sample" refers to a cell or population of cells or a quantity of tissue or fluid from a subject. Most often, the sample has been removed from a subject, but the term "biological sample" can also refer to cells or tissue analyzed in vivo, i.e. without removal from the subject. Often, a "biological sample" will contain cells from the subject, but the term can also refer to non-cellular biological material, such as non-cellular fractions of blood, saliva, or urine, that can be used to measure gene expression levels. Biological samples include, but are not limited to, tissue biopsies, needle biopsies, scrapes (e.g. buccal scrapes), whole blood, plasma, serum, lymph, bone marrow, urine, saliva, sputum, cell culture, pleural fluid, pericardial fluid, ascitic fluid or cerebrospinal fluid. Biological samples also include tissue biopsies and cell cultures. A biological sample or tissue sample can refer to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the sample is from a resection, bronchoscopic biopsy, or core needle biopsy of a primary or metastatic tumor, or a cellblock from pleural fluid. In addition, fine needle aspirate samples can be used. Samples may be paraffin-embedded or frozen tissue. The sample can be obtained by removing a sample of cells from a subject, but can also be accomplished by using previously isolated cells (e.g. isolated by another person), or by performing the methods of the invention in vivo.

The term "coupled to" as used herein is intended to encompass any construction whereby the RNA aptamer is linked, attached or joined to a detection agent, moiety, siRNA or ribozyme as described herein. Methods for effecting coupling will be known to persons skilled in the art and include, but are not limited to conjugation, linking via peptide linker or by direct chemical synthesis of the RNA and agent (e.g. siRNA or ribozyme) as a whole chain.

The term "isolated" as used herein is intended to refer to the RNA aptamer or the stem cell (e.g. cancer stem cell), isolatable or purified from other components. An isolated cell refers to a cell from the environment in which it may naturally occur. The isolated cell may be purified to any degree relative to its naturally-obtainable state.

The term "ligand" as used herein refers to a molecule or other chemical entity having a capacity for binding to a target. A ligand can comprise a peptide, an oligomer, a nucleic acid (e.g. an aptamer), a small molecule (e.g. a chemical compound), an antibody or fragment thereof, nucleic acid-protein fusion and/or any other affinity agent.

Thus, a ligand can come from any source, including libraries, particularly combinatorial libraries, such as the aptamer libraries disclosed herein below, phage display libraries, or any other library as would be apparent to one of ordinary skill in the art after review of the disclosure herein.

The term "modified RNA aptamer" as used herein is meant to refer to a polymeric molecule, which in addition to containing ribonucleosides as its units, also contains at least one of the following: 2'-deoxy, 2'-halo (including 2'-fluoro), 2'-amino (preferably not substituted or mono- or disubstituted), 2'-mono-, di- or tri-halomethyl, 2'-O-alkyl, 2'-O-halo-substituted alkyl, 2'-alkyl, azido, phosphorothioate, sulfhydryl, methylphosphonate, fluorescein, rhodamine, pyrene, biotin, xanthine, hypoxanthine, 2,6-diamino purine, 2-hydroxy-6-mercaptopurine and pyrimidine bases substituted at the 6-position with sulfur or 5 position with halo or $C_{15}$ alkyl groups, abasic linkers, 3'-deoxy-adenosine as well as other available "chain terminator" or "non-extendible" analogs (at the 3'-end of the RNA), or labels such as $^{32}P$, $^{33}P$ and the like. All of the foregoing can be incorporated into an RNA using the standard synthesis techniques disclosed herein.

As used herein, the term "therapeutically effective amount" shall be taken to mean a sufficient quantity of RNA aptamer, anticancer agent, delivery agent or pharmaceutical composition according to the present disclosure to reduce or inhibit the number of CD133 expressing cancer stem cells and/or one or more symptoms of cancer. The skilled artisan will be aware that such an amount will vary depending upon, for example, the particular subject and/or the type or severity or level of disease. The term is not be construed to limit the present disclosure to a specific quantity of RNA aptamer.

As used herein, the term "treat" or "treatment" or "treating" shall be understood to mean administering a therapeutically effective amount of RNA aptamer, anticancer agent, delivery agent or pharmaceutical composition as disclosed herein and reducing or inhibiting at least one symptom of a clinical condition associated with or caused by cancer.

As used herein, the term "prevent" or "preventing" or "prevention" shall be taken to mean administering a therapeutically effective amount of RNA aptamer, anticancer agent, delivery agent or pharmaceutical composition according to the present disclosure and stopping or hindering or delaying the development or progression of at least one symptom of cancer.

As used herein, the term "specifically binds" shall be taken to mean that the RNA aptamer reacts or associates more frequently, more rapidly, with greater duration and/or with greater affinity with a particular cell or substance than it does with alternative cells or substances. For example, an RNA aptamer that specifically binds to a target protein binds that protein or an epitope or immunogenic fragment thereof with greater affinity, avidity, more readily, and/or with greater duration than it binds to unrelated protein and/or epitopes or immunogenic fragments thereof. It is also understood by reading this definition that, for example, a RNA aptamer that specifically binds to a first target may or may not specifically bind to a second target. As such, "specific binding" does not necessarily require exclusive binding or non-detectable binding of another molecule, this is encompassed by the term "selective binding". Generally, but not necessarily, reference to binding means specific binding. The specificity of binding is defined in terms of the comparative dissociation constants (Kd) of the aptamer for target as compared to the dissociation constant with respect to the aptamer and other materials in the environment or unrelated molecules in general. Typically, the Kd for the aptamer with respect to the target will be 2-fold, 5-fold, or 10-fold less than the Kd with respect to the target and the unrelated material or accompanying material in the environment. Even more preferably, the Kd will be 50-fold, 100-fold or 200-fold less.

The term "CD133$^+$" or "CD133 expressing cell" as used herein may be used interchangeably. The term encompasses cell surface expression of the CD133 antigen which can be detected by any suitable means. In one example, reference to a cell being positive for a given marker means it may be either a low (lo or dim) or a high (bright, bri) expresser of that marker depending on the degree to which the marker is present on the cell surface, where the terms relate to intensity of fluorescence.

As used herein, the term "subject" shall be taken to mean any subject, including a human or non-human subject. The non-human subject may include non-human primates, ungulate (bovines, porcines, ovines, caprines, equines, buffalo and bison), canine, feline, lagomorph (rabbits, hares and pikas), rodent (mouse, rat, guinea pig, hamster and gerbil), avian, and fish. In one example, the subject is a human.

Aptamers

Several unique properties of aptamers make them attractive tools for use in a wide array of molecular biology applications, and as potential pharmaceutical agents. First, most aptamers bind to targets with high affinity, demonstrating typical dissociation constants in the pico- to nanomolar range. Binding sites for aptamers include clefts and grooves of target molecules resulting in antagonistic activity very similar to many currently available pharmaceutical agents. Second, aptamers are structurally stable across a wide range of temperature and storage conditions, maintaining the ability to form their unique tertiary structures. Third, aptamers can be chemically synthesised, in contrast to the expensive and work-intensive biological systems needed to produce monoclonal antibodies.

Without wishing to be bound by theory, RNA aptamers are generally preferred by many groups due to the theoretically higher affinity of RNA aptamers for their target proteins as well as the greater plasma stability of modified RNA than unmodified RNA.

Disclosed herein are RNA aptamer molecules that specifically bind to the CD133 antigen which can be used for effective intracellular delivery of siRNA or ribozyme, chemotherapy drugs, radioisotopes, toxins and/or other agents bearing the antigen.

Aptamers are single stranded oligonucleotides or oligonucleotide analogs that bind to a particular target molecule, such as a protein or a small molecule. Thus, aptamers are the oligonucleotide analogy to antibodies. In general, aptamers comprise about 15 to about 100 nucleotides, preferably about 15 to about 40 nucleotides, and more preferably about 20 to about 40 nucleotides, in that oligonucleotides of a length that falls within these ranges can be prepared by conventional techniques. Optionally, aptamers can further comprise a minimum of approximately 6 nucleotides, preferably 10, and more preferably 14 or 15 nucleotides, that are necessary to effect specific binding. Aptamers of binding regions containing sequences shorter than 10, e.g., 6-mers, are feasible if the appropriate interaction can be obtained in the context of the environment in which the target is placed. Thus, if there is little interference by other materials, less specificity and less strength of binding can be required.

Aptamer binding is highly dependent on the secondary structure formed by the aptamer oligonucleotide. Both RNA and single stranded DNA (or analog) aptamers are known.

See, for example, Burke et al (1996). J. Mol. Biol. 264:650-666; Ellington and Szostak (1990). Nature 346:818-22; Hirao et al (1998). Mol Divers. 4:75-89; Jaeger et al (1998). EMBO Journal 17:4535; Kensch et al (2000). J. Biol. Chem 275:18271-8; Schneider et al (1995). Biochemistry 34:9599-9610; and U.S. Pat. No. 5,773,598; U.S. Pat. No. 6,028,186; U.S. Pat. No. 6,110,900; U.S. Pat. No. 6,127,119; and U.S. Pat. No. 6,171,795.

Selection of Aptamers for a Given Target

Aptamers that bind to virtually any particular target can be selected by using an iterative process called SELEX™ (Systemic Evolution of Ligands by EXponential Enrichment). The process is described in, for example U.S. Pat. No. 5,270,163 and U.S. Pat. No. 5,475,096. The SELEX™ process is based on the unique insight that nucleic acids have sufficient capacity for forming a variety of two- and three-dimensional structures and sufficient chemical versatility available within their monomers to act as ligands (i.e., form specific binding pairs) with virtually any chemical compound, whether monomeric or polymeric. Molecules of any size or composition can serve as targets.

The SELEX™ process relies, as a starting point, upon a large library or pool of single stranded oligonucleotides comprising randomised sequences. The oligonucleotides can be modified or unmodified DNA, RNA, or DNA/RNA hybrids. In some examples, the pool comprises 100% random or partially random oligonucleotides. In other examples, the pool comprises random or partially random oligonucleotides containing at least one fixed sequence and/or conserved sequence incorporated within randomized sequence. In other examples, the pool comprises random or partially random oligonucleotides containing at least one fixed sequence and/or conserved sequence at its 5' and/or 3' end which may comprise a sequence shared by all the molecules of the oligonucleotide pool. Fixed sequences are sequences common to oligonucleotides in the pool which are incorporated for a preselected purpose such as, CpG motifs, hybridization sites for PCR primers, promoter sequences for RNA polymerases (e.g., T3, T4, T7, and SP6), restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool preferably include a randomised sequence portion as well as fixed sequences necessary for efficient amplification. Typically, the oligonucleotides of the starting pool contain fixed 5' and 3' terminal sequences which flank an internal region of 30-50 random nucleotides. The randomised nucleotides can be produced in a number of ways including chemical synthesis and size selection from randomly cleaved cellular nucleic acids. Sequence variation in the test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs (see for example U.S. Pat. No. 5,958,691, U.S. Pat. No. 5,660,985 and WO 92/07065). Random oligonucleotides can be synthesized from phosphodiester-linked nucleotides using solid phase oligonucleotide synthesis techniques well known in the art. See, for example, Froehler et al., (1986). Nucl. Acid Res. 14:5399-5467 and Froehler et al (1986) Tet. Lett. 27:5575-5578. Random oligonucleotides can also be synthesized using solution phase methods such as triester synthesis methods. See, e.g., Sood et al (1977). Nucl. Acid Res. 4:2557 and Hirose et al (1978). Tet. Lett., 28:2449. Typical syntheses carried out on automated DNA synthesis equipment yield $10^{14}$-$10^{16}$ individual molecules, a number sufficient for most SELEX™ experiments.

The starting library of oligonucleotides may be generated by automated chemical synthesis on a DNA synthesiser. Partially random sequences can be created by adding the four nucleotides in different molar ratios at each addition step.

The starting library of oligonucleotides may be either RNA or DNA. In those instances where an RNA library is to be used as the starting library it is typically generated by transcribing a DNA library in vitro using T7 RNA polymerase or modified T7 RNA polymerases and purified. The RNA or DNA library is then mixed with the target under conditions favourable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favourable for binding; (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX™ method further comprises the steps of: (i) reverse transcribing the nucleic acids dissociated from the nucleic acid-target complexes before amplification in step (d); and (ii) transcribing the amplified nucleic acids from step (d) before restarting the process.

Cycles of selection and amplification are repeated until a desired goal is achieved. Generally this is until no significant improvement in binding strength is achieved on repetition of the cycle. Typically, nucleic acid aptamer molecules are selected in a 5 to 20 cycle procedure.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX™ procedures with contiguous randomized segments be initiated with nucleic acid sequences containing a randomized segment of between about 20 to about 50 nucleotides.

The core SELEX™ method has been modified to achieve a number of specific objectives. For example, U.S. Pat. No. 5,707,796 describes the use of SELEX™ in conjunction with gel electrophoresis to select nucleic acid molecules with specific structural characteristics, such as bent DNA. U.S. Pat. No. 5,763,177 describes SELEX™ based methods for selecting nucleic acid ligands containing photo reactive groups capable of binding and/or photo-crosslinking to and/or photo-inactivating a target molecule. U.S. Pat. No. 5,567,588 and U.S. Pat. No. 5,861,254 describe SELEX™ based methods which achieve highly efficient partitioning between oligonucleotides having high and low affinity for a target molecule. U.S. Pat. No. 5,496,938 describes methods for obtaining improved nucleic acid ligands after the SELEX™ process has been performed. U.S. Pat. No. 5,705,337 describes methods for covalently linking a ligand to its target.

Counter-SELEX™ is a method for improving the specificity of nucleic acid ligands to a target molecule by eliminating nucleic acid ligand sequences with cross-reactivity to one or more non-target molecules. Counter-SELEX™ is comprised of the steps of: (a) preparing a candidate mixture of nucleic acids; (b) contacting the candidate mixture with the target, wherein nucleic acids having an increased affinity to the target relative to the candidate mixture may be partitioned from the remainder of the candidate mixture; (c) partitioning the increased affinity nucleic acids from the remainder of the candidate mixture; (d) dissociating the increased affinity nucleic acids from the target; (e) contacting the increased affinity nucleic acids with one or more non-target molecules such that nucleic acid ligands with specific affinity for the non-target molecule(s) are removed; and (f) amplifying the nucleic acids with specific affinity only to the target molecule to yield a mixture of nucleic acids enriched for nucleic acid sequences with a relatively higher affinity and specificity for binding to the target molecule. As described above for SELEX™, cycles of selection and amplification are repeated as necessary until a desired goal is achieved.

In a representative example, an RNA aptamer is synthesized on a solid support column, using conventional techniques such as those described by Beaucage et al. (1981) Tetrahedr. Letters 22:1859-1862 and Sinha et al., (1984) Nucleosides and Nucleotides 3:157-171. The final DMT-group is removed from the resulting RNA aptamer. Alternately, if large-scale synthesis is used, the RNA aptamer can be made by scale-up of the solid support method or the RNA aptamer can be made by using solution phase techniques, particularly if the desired end-product is a relatively short oligonucleotide. A starting material for the synthesis process can be a 5'-non-tritylated RNA oligoribo-nucleotide or analog of the desired primary structure, which preferably can have protected bases, and which is preferably bound to a solid-support. Any conventionally used protecting groups can be used. Typically $N_6$-benzoyl is used for adenine, $N_4$-benzoyl for cytosine, $N_2$-isobutyryl for guanine and $N_2$-benzoyl for 2-amino purine. Other useful protecting groups include phenoxyacetyl (PAC) and t-butoxyacetyl (TAC). Conveniently, the more base labile protection groups should be used for the synthesis of the RNA aptamer; those of ordinary skill in the art know these groups. Such groups can help to prevent hydrolysis of the generated tri- or diphosphates, which are generally quite stable under basic conditions, but could be subject to some hydrolysis. Other envisioned modifications are disclosed in U.S. Pat. No. 6,011,020, and include but are not limited to the incorporation of bioavailability enhancing molecules such as PEG or cholesterol via a covalent linkage.

In addition, nucleoside analogs such as 2'-deoxy, 2'-halo, 2'-amino (not substituted or mono- or disubstituted), 2'-mono, di- or trihalomethyl, 2'-O-alkyl, 2'-O-halo-substituted alkyl, 2'-alkyl, azido, phosphorothioate, sulfhydryl, methylphosphonate, fluorescein, rhodamine, pyrene, biotin, xanthine, hypoxanthine, 2,6-diamino purine, 2-hydroxy-6-mercaptopurine and pyrimidine bases substituted at the 6-position with sulfur or 5 position with halo or $C_{1-5}$ alkyl groups, abasic linkers, 3'-deoxy-adenosine as well as other available "chain terminator" or "non-extendible" analogs (at the 3'-end of the RNA), and the like can be incorporated during the RNA synthesis. Further, various labels such as $^{32}P$ or $^{33}P$ and the like can likewise be incorporated during the synthesis, resulting in novel RNA analogs produced by this process. Other envisioned modifications are disclosed in U.S. Pat. No. 6,011,020, and include but are not limited to the incorporation of 3' caps, such an inverted DT cap, or an inverted abasic cap, or combination thereof.

Binding Affinity of Aptamers

The binding affinity describes the measure of the strength of the binding or affinity of molecules to each other. Binding affinity of the aptamer herein with respect to targets and other molecules is defined in terms of $K_d$. The dissociation constant can be determined by methods known in the art and can be computed even for complex mixtures by methods such as those, for example, set forth in Caceci, M., et al., *Byte* (1984) 9:340-362. Examples of measuring dissociation constants are described for example in U.S. Pat. No. 7,602,495 which describes surface Plasmon resonance analysis, U.S. Pat. No. 6,562,627, U.S. Pat. No. 6,562,627, and US 2012/00445849. In another example, the $K_d$ is established using a double-filter nitrocellulose filter binding assay such as that disclosed by Wong and Lohman, (1993). *Proc. Nati. Acad. Sci. USA* 90, 5428-5432.

It has been observed, however, that for some small oligonucleotides, direct determination of $K_d$ is difficult, and can lead to misleadingly high results. Under these circumstances, a competitive binding assay for the target molecule or other candidate substance can be conducted with respect to substances known to bind the target or candidate. The value of the concentration at which 50% inhibition occurs $(K_i)$ is, under ideal conditions, equivalent to $K_d$. However, in no event will a $K_i$ be less than $K_d$. Thus, determination of $K_i$, in the alternative, sets a maximal value for the value of $K_d$. Under those circumstances where technical difficulties preclude accurate measurement of $K_d$, measurement of $K_i$ can conveniently be substituted to provide an upper limit for $K_d$. A $K_i$ value can also be used to confirm that an aptamer of the present binds a target.

Improving Aptamer Stability

One potential problem encountered in the use of nucleic acids as therapeutics in that oligonucleotides in their phosphodiester form may be quickly degraded in body fluids by intracellular and extracellular enzymes such as endonucleases and exonucleases before the desired effect is manifest. The present disclosure also includes RNA analogs as described herein and/or additional modifications designed to improve one or more characteristics of the RNA aptamer such as protection from nuclease digestion.

Oligonucleotide modifications contemplated in the present disclosure include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole.

Modifications to generate oligonucleotides which are resistant to nucleases can also include one or more substitute internucleotide linkages, altered sugars, altered bases, or combinations thereof. Such modifications include 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, and unusual base-pairing combinations such as the isobases isocytidine and isoguanosine; 3' and 5' modifications such as capping; conjugation to a high molecular weight, non-immunogenic compound; conjugation to a lipophilic compound; and phosphate backbone modification.

In one example, the non-immunogenic, high molecular weight compound conjugated to the aptamer of the present disclosure is polyalkylene glycol, preferably polyethylene glycol. In one example, the backbone modification comprises incorporation of one or more phosphorothioates into the phosphate backbone. In another example, the aptamer of the present disclosure comprises the incorporation of fewer than 10, fewer than 6, or fewer than 3 phosphorothioates in the phosphate backbone.

Utility of the Aptamers

The RNA aptamer molecules of the present disclosure can be used as affinity ligands to separate and purify target molecules (e.g. CD133 bearing cancer stem cells), as probes to trace, monitor, detect and quantitate target molecules (e.g. CD133 bearing cancer stem cells), or to block, allow, activate or catalyse reactions that are physiologically relevant to achieve therapeutic effect. They can act as pharmaceutical agent, bind to a specific target and direct specific molecules to a desired site.

The RNA aptamer molecules of the present disclosure can be used in in vitro processes, for example affinity purification mixtures to purify target molecules (e.g. CD133 bearing cancer stem cells). The aptamers are ideal for chromatographic separations of target molecules (e.g. CD133 bearing cancer stem cells) from contaminants and for purifying target molecules from cell cultures or cell extracts.

In one example, the RNA aptamer molecules of the present disclosure can be used as a capture agent to bind or immobilise a target (e.g. CD133 bearing cancer stem cells) to a solid support. The solid support can be comprised of substrates having the structure and composition commonly associated with filters, wafers, wafer chips, membranes and thin films. However, it is contemplated that the solid support may be comprises of substrates including, but not limited to resins, affinity resins, magnetic or polymer beads, or any diagnostic detection reagent, to capture or immobilise reagents for diagnostic, detection or quantitative studies, The solid supports may comprise any material depending of the desired use, including but not limited to glass, metal surfaces and materials such as steel, ceramic or polymeric materials such as polyethylene, polypropylene, polyamide, and polyvinylidenefluoride etc or combinations thereof.

CD133 Antigen

CD133, originally known as AC133 is a glycoprotein (also known as Prominin 1). It is a member of pentaspan transmembrane glycoproteins which specifically localise to cellular protrusions. CD133 is expressed in hematopoietic stem cells, endothelial progenitor cells, gliobalstoma, neuronal and glial stem cells, carious pediatric brain tumors, as well as adult kidney, mammary glands, trachea, salivary glands, placenta, digestive tract, testes and other cell types.

Isolation and Purification of CD133 Expressing Cancer Stem Cells

The best known example of adult cell renewal by the differentiation of stem cells is the hematopoietic system. Developmentally immature precursors such as hematopoietic stem cells and progenitor cells respond to molecular signals to gradually form the varied blood and lymphoid cell types. Stem cells are also found in other tissues, including epithelial tissues and mesenchymal tissues. Cancer stem cells may arise from any of these cell types, for example, as a result of genetic damage in normal stem cells or by the dysregulated proliferation of stem cells and/or differentiated cells.

Cancer stem cells may be derived from any cancer comprising tumorigenic stem cells, i.e. cells having an ability to proliferate extensively or indefinitely, and which give rise to the majority of cancer cells. Within an established tumor, most cells have lost the ability to proliferate extensively and form new tumors, and a small subset of cancer stem cells proliferate to thereby regenerate the cancer stem cells as well as give rise to tumor cells lacking tumorigenic potential. Cancer stem cells may divide asymmetrically and symmetrically and may show variable rates of proliferation. Cancer stem cell may include transit amplifying cells or progenitor cells that have reacquired stem cell properties.

Representative cancers from which stem cells may be isolated include cancers characterised by solid tumors, including for example fibrosarcoma, myxosarcoma, liposarcoma, chondrosarcoma, osteogenic sarcoma, chordoma, angiosarcoma, endotheliosarcoma, lymphangiosarcoma, synovioma, lymphagioendotheliosarcoma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma and retinoblastoma.

Additional representative cancers from which stem cells can be isolated or enriched according to the present disclosure include hematopoietic malignancies, such as B cell lymphomas and leukemias, including low grade/follicular non-Hodgkin's lymphoma (NHL), small lymphocytic (SL) NHL, intermediate grade/follicular NHL, intermediate grade diffuse NHL, high grade immunoblastic NHL, high grade small non-cleaved cell NHL, bulky disease NHL and Waldenstrom's Macroglobulinemia, chronic leukocytic leukemia, acute myelogenous leukemia, chronic myelogenous leukemia, lymphoblastic leukemia, lymphocytic leukemia, monocytic leukemia, myelogenous leukemia and promyelocytic leukemia.

Cancer stem cells bearing CD133 may be selected using the aptamer molecules as described herein. For example, aptamers which are coupled to fluorescent dyes can be used for the positive selection of cancer stem cells. CD133 is also known to be expressed in some normal cells. However, CD133 expression is thought to be upregulated in cancer stem cells. Cancer stem cell markers are typically expressed at a level that is at least about 5-fold greater than differentiated cells of the same origin or non-tumorigenic cells, for example, at least about 10-fold greater, or at least about 15-fold greater, or at least about 20-fold greater, or at least about 50-fold greater, or at least about 100-fold greater. The selection process may also include negative selection markers which can be used for the elimination of those cancer cells in the population that are not cancer stem cells.

It will be understood that in performing the present disclosure, separation of cells bearing CD133 can be effected by a number of different methods. For example, the RNA aptamer of the present disclosure may be attached to a solid support to allow for a crude separation. Various techniques of different efficacy may be employed depending upon efficiency of separation, associated cytotoxicity, ease and speed of performance and necessity for sophisticated equipment and/or technical skill. Procedures for isolation or purification may include, but are not limited to, magnetic separation using aptamer-coated magnetic beads, affinity chromatography and "panning" with aptamer attached to a solid matrix. Techniques providing accurate isolation or purification include but are not limited to FACS. Methods for preparing FACS will be apparent to the skilled artisan.

Enrichment of CD133 Expressing Cancer Stem Cells

In one example, the RNA aptamer molecules of the present disclosure are enriched from a biological sample obtained from a subject. Typically the subject will be one which has a tumor or is suspected of having a tumor containing cancer stem cells. The term "enriched" or "enrichment" or variations thereof are used herein to describe a population of cells in which the proportion of one particular cell type (i.e. cancer stem cells) is increased when compared with an untreated population of the cells (e.g. cells in the sample).

In one example, a population enriched for cancer stem cells comprises at least about 0.1%, or 0.5% or 1% or 2% or 5% or 10% or 15% or 20% or 25% or 30% or 50% or 75% CD133 bearing cancer stem cells. In this regard, the term "enriched cell population comprising cancer stem cells" will be taken to provide explicit support for the term "population of cells comprising X % cancer stem cells, wherein X % is a percentage as recited herein.

In one example, the population of cells is enriched from a cell preparation comprising CD133+ cells in a selectable form. In this regard, the term "selectable form" will be understood to mean that the cells express a marker (e.g. a cell surface marker) permitting selection of CD133 bearing cells.

Diagnosis of Cancer Using Aptamer Molecules

The RNA aptamer molecules of the present disclosure can be used in vitro for diagnostic purposes to determine the presence of cancer stem cells in malignant tissue. The method involves examining a biological sample for the presence of CD133+ cancer stem cells. For example, the biological sample can be contacted with a labelled RNA aptamer of the present disclosure and the ability of the RNA aptamer to specifically bind to the cells in the sample is determined. Binding indicates the presence of a CD133 bearing cancer stem cell. The RNA aptamer of the present disclosure can also be used to localise a tumor in vivo by administering to a subject an isolated RNA aptamer of the present disclosure which is labelled with a reporter group which gives a detectable signal. Bound aptamers can then be detected using flow cytometry, microscopy, external scintigraphy, emission tomography, optical imaging or radionuclear scanning. The method can be used to stage a cancer in a subject with respect to the extent of the disease and to monitor changes in response to therapy.

Detection of cancer stem cells can be facilitated by coupling the RNA aptamer to a detectable label. Examples of detectable labels include various enzymes, prosthetic groups, fluorescent materials, luminescent materials, bioluminescent materials, electron dense labels, labels for MRI, and radioactive materials. Examples of suitable enzymes include horseradish peroxidise, alkaline phosphatise, β-galactosidase, or acetylcholinesterase. Examples of suitable prosthetic group complexes include streptavidin/biotin and avidin/biotin. Examples of suitable fluorescent materials include umbellifone, fluorescein isothiocyanate, rhodamine, dischlorotriazinylamine fluorescein, dansyl chloride or phycoerythrin. An example of a luminescent material includes luminol. Examples of bioluminescent materials include luciferase, luciferin, and aequorin, and examples of suitable radioactive material include $^{125}$I, $^{131}$I, $^{35}$S, $^{18}$F, $^{64}$Cu, $^{94m}$-Tc, $^{124}$I, $^{11}$C, $^{13}$N, $^{15}$O, $^{68}$Ga, $^{86}$Y, $^{82}$Rb or $^{3}$H.

Labelling at the 3' end of the aptamer can be achieved, for example by templated extension using Klenow polymerase, by T4 RNA ligase-mediated ligation and by terminal deoxynucleotidyl transferase. Labelling at the 5' end can be achieved by the supplementation of the in vitro transcription mix with an excess of GTP-β-S, the thiol of which can then be used to attach biotin. In addition, direct chemical conjugation of a suitable group(s) to either 5'- or 3'-end can be used to label the aptamers.

Anticancer Agent of the Present Disclosure

The RNA aptamer molecules of the present disclosure can be conjugated to a moiety and used to direct the moiety to CD133+ cells, preferably cancer stem cells. Examples of moieties include toxins, radionuclides, or chemotherapeutic agents which can be used to kill cancer stem cells.

The RNA aptamer can be fused to the moiety, e.g. the toxin, either by virtue of the moiety and aptamer being chemically synthesised, or by means of conjugation, e.g. a non-peptide covalent bond, e.g. a non-amide bond, which is used to join separately produced RNA aptamer and the moiety. Alternatively, the RNA aptamer and moiety may be joined by virtue of a suitable linker peptide.

Useful toxin molecules include peptide toxins, which are significantly cytotoxic when present intracellularly. Examples of toxins include cytotoxins, metabolic disrupters (inhibitors and activators) that disrupt enzymatic activity and thereby kill cancer stem cells, and radioactive molecules that kill all cells within a defined radius of the effector portion. A metabolic disrupter is a molecule, e.g. an enzyme or a cytokine that changes the metabolism of a cell such that is normal function is altered. Broadly, the term toxin includes any effector that causes death to a tumor cell.

Many peptide toxins have a generalised eukaryotic receptor binding domain; in these instances the toxin must be modified to prevent killing cells not bearing CD133 (e.g. to prevent killing cells not bearing CD133 but having a receptor for the unmodified toxin). Such modifications must be made in a manner that preserves the cytotoxic function of the molecule. Potentially useful toxins include, but are not limited to diphtheria toxin, cholera toxin, ricin, 0-Shiga-like toxin (SLT-I, SLT-II, SLT-II$_V$), LT toxin, C3 toxin, Shiga toxin pertussis toxin, tetanus toxin, *Pseudomonas* exotoxin, alorin, saponin, modeccin and gelanin. Other toxins include tumor necrosis actor alpha (TNF-alpha) and lymphotoxin (LT). Another toxin which has antitumor activity is calicheamicin gamma 1, a diyne-ene containing antitumor antibiotic with considerable potency against tumors (Zein N et al (1988). Science 240:1198-201).

As an example, diphtheria toxin (which sequence is known) can be conjugated to the RNA aptamer molecules of the present disclosure. The natural diphtheria toxin molecule secreted by *Corynebacterium diptheriae* consist of several functional domains that can be characterised, starting at the amino terminal end of the molecule, as enzymatically-active fragment A (AA 1-193) and fragment B (AA 194-535) which includes a translocation domain and a generalised cell binding domain (AA 475-535).

The RNA aptamer and the toxin moiety can be linked in any of several ways which will be known to persons skilled in the art. For example, a method of conjugating an RNA aptamer to a toxin (gelonin) is described in Chu T C et al. (2006) Cancer Res 6(12)5989-5992.

The moiety can also be a modulator of the immune system that either activates or inhibits the body's immune system at the local level. For example, cytokines e.g. lymphokines such as IL-2, delivered to a tumor can cause the proliferation of cytotoxic T-lymphocytes or natural killer cells in the vicinity of the tumor.

The moiety or reporter group can also be a radioactive molecule, e.g. a radionucleotide, or a so-called sensitizer, e.g. a precursor molecule that becomes radioactive under specific conditions, e.g. boron when exposed to a bean of low-energy neutrons, in the so-called "boron neutron capture therapy" (BNCT) as described in Barth et al. (1990). Scientific American Oct 1990:100-107. Compounds with such radioactive effector portions can be used both to inhibit proliferation of cancer stem cells in the tumor and to label the cancer stem cells for imaging purposes.

Radionucleotides are single atom radioactive molecules that can emit either α, β, or γ particles. Alpha particle emitters are preferred to β, or γ particle emitters, because they release far higher energy emissions over a shorter distance, and are therefore efficient without significantly penetrating, and harming, normal tissues. Suitable α particle emitting radionuclides include $^{211}$At, $^{212}$Pb, and $^{212}$Bi.

The radioactive molecule must be tightly linked to the aptamer either directly or by a bifunctional chelate. This chelate must not allow elution and thus premature release of the radioactive molecule in vivo. Waldmann, Science, 252: 1657-62 (1991). As an example, to adapt BNCT to the present invention, a stable isotope of boron, e.g., boron 10, can be selected as the antitumor moiety or effector portion of the compound. The boron will be delivered to and concentrates in or on the tumor cells by the specific binding of the aptamer to the cancer stem cell. After a time that allows a sufficient amount of the boron to accumulate, the tumor can be imaged and irradiated with a beam of low-energy neutrons, having an energy of about 0.025 eV. While this neutron irradiation, by itself, causes little damage to either the healthy tissue surrounding the tumor, or the tumor itself, boron 10 (e.g., on the surface of a tumor cell) will capture the neutrons, thereby forming an unstable isotope, boron 11. Boron 11 instantly fissions yielding lithium 7 nuclei and energetic α particles, about 2.79 million Ev. These heavy particles are a highly lethal, but very localized, form of radiation, because particles have a path length of only about one cell diameter (10 microns).

Delivery Agent of the Present Disclosure

The RNA aptamer molecules of the present disclosure can be used for siRNA or ribozyme delivery into cells. Examples of suitable siRNA or ribozyme will depend upon the circumstances. Examples of siRNAs or ribozymes that are suitable for use according to the present disclosure include those which target ATP binding cassette membrane transporters, stemness genes (Bmi-1, Notch 1, Sox 2, Oct-4, Nanog, β-catenin, Smo, nestin, ABCG2, Wnt2 and SCF, etc), GAPDH (glyceraldehyde 3-phosphate dehydrogenase), and survivin.

By way of example, this has been demonstrated in the prior art using an anti-PSMA aptamer. Based on the knowledge that PSMA is internalised via clathrin-coated pits to endosome, it was postulated that the anti-PSMA aptamer would carry the attached siRNA to the cells that express PSMA, and the aptamer-siRNA bound to the PSMA protein would gain access to the cell via internalisation. Next, the siRNA portion would undergo processing by the Dicer complex and feed into the RNA-Induced Silencing Complex (RISC)-mediated gene-silencing pathway. Three groups have utilised different strategies to accomplish this. Chu et al (2006) Nucleic Acids Res 34, e73 describes a biotin-streptavidin bridge mediated conjugation method to assemble the anti-PSMA aptamer and the siRNA. McNamara et al. (2006) Nat Biotechnol 24, 1005-1015 used a "RNA-only" aptamer-siRNA chimera approach to link the aptamer and the siRNA. In a subsequent study by Wullner et al (2008). Curr. Cancer Drug Targets 8:554-565, the authors used the anti-PSMA aptamer to deliver Eukaryotic Elongation Factor 2 (EEF2) siRNA to PSMA-positive prostate cancer cells, Bivalent PSMA aptamers were used for this purpose. The authors demonstrated that, compared to the monovlaent anti-PSMA-siRNA chimera, the gene knockdown potency of the bivalent aptamer-construct was superior.

The RNA aptamer molecules of the present disclosure can also be used to deliver cargo into CD133$^+$ cancer stem cells in a variety of solid tumours. Gelonin is a ribosomal toxin that can inhibit the process of protein synthesis and is cytotoxic. However, it is membrane impermeable and needs an usher for its cellular entry. Thus, the RNA aptamer molecules of the present disclosure can be utilised to deliver membrane impermeable toxic payload to cancer stem cells.

Tumor resistance to cytotoxic chemotherapeutic agents is due in part to insufficient delivery to and uptake, and more importantly, efflux by cancer cells. Biodegradable nanoparticle (NP) derived from poly(D,L-lactic-co-glycolic acid) PLGA were used to address this problem as described in Dhar et al (2008) Proc. Natl. Acad. Sci. USA 105:17356-17361. Briefly, cisplatin was converted to its pro-drug, Pt(IV) compound, by introducing two alkyl chains. This increased the hydrophobicity of the compound and eased the process of its packaging within the hydrophobic core of the NP. Polyethylene glycol (PEG) was used as a copolymer during the nanoprecipitation step to synthesise the PLGA-PEG nanoparticle. The PLGA-PEG-NP surface was decorated with a PSMA (prostate specific membrane antigen) aptamer. The NP underwent endocytosis when incubated with LNCaP cells, and the alkylated pro-drug was converted to cisplatin by the cytosolic reduction process.

The present disclosure also extends to the use of the RNA aptamer molecules as simultaneous drug delivery and imaging agents. This can be achieved by conjugating the aptamer to the surface of a fluorescent quantum dot (QD). Next, the QD-aptamer conjugate is incubated with Dox to form the QD-aptamer-Dox nanoparticle. Both Dox and QD are fluorescent molecules. However, due to their proximity in the QD-aptamer-Dox nanoparticle, they quench each other's fluorescence by a bi-fluorescence resonance energy transfer (FRET) mechanism. Thus, the QD-aptamer-Dox nanoparticle is non-fluorescent. However, internalisation of the QD-aptamer-Dox nanoparticle via PSMA-mediated endocytosis in prostate cancer cells causes the release of Dox from the QD-aptamer-Dox nanoparticles, that results in the recovery of fluorescence by both Dox and QD.

Pharmaceutical Compositions

In one example of the present disclosure the RNA aptamer, anticancer agent or drug delivery agent according to the present disclosure is administered in the form of a composition comprising a pharmaceutically acceptable carrier and/or excipient. The choice of excipient or other elements of the composition can be adapted in accordance with the route and device used for administration.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for the present disclosure include those conventionally used, e.g. water, saline, aqueous dextrose, lactose, Ringer's solution a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

Other general additives such as anti-oxidative agent, buffer solution, bacteriostatic agent etc can be added. In order to prepare injectable solutions, pills, capsules, granules, or tablets, diluents, dispersing agents, surfactants, binders and lubricants can be additionally added.

The anticancer agent or drug delivery agent containing the RNA aptamer of the present invention can be administered parentally (for example, intravenous, hypodermic, local or peritoneal injection). The effective dosage of the anticancer agent can be determined according to weight, age, gender, health condition, diet, administration frequency, administration method, excretion and severity of a disease. In one example, the anticancer agent or drug delivery agent contains the RNA aptamer by 10-95 weight %. In another example, the anticancer agent or drug delivery agent contains the RNA aptamer by 25-75 weight %.

The administration frequency may be one to several times a day.

In one example, the effective intracellular content of the RNA aptamer is approximately 1 nM to 1000 nM. In another example, the effective intracellular content of the RNA aptamer is preferably 100 nM to 500 nM. However, the dosage of the aptamer could be under or more than the above range.

Combinations of Aptamers

The isolated RNA aptamer molecule(s) of the present disclosure can be used alone or in combination with one or more additional RNA aptamers according to any method disclosed herein. In one example, the RNA aptamer molecule(s) of the present disclosure can be combined with an RNA aptamer that facilitates the detection, purification or enrichment of cancer stem cells. In one example, the additional RNA aptamer comprises the sequence of aptamer EpDT3 5'-GCGACUGGUUACCCGGUCG-3' (SEQ ID NO: 9) as described in Shigdar S et al (2011). Cancer Sci 102(5):991-998. In another example, the additional RNA aptamer comprises the sequence 5'-ACGUAUC-CCUUUUCGCGUA-3' (SEQ ID NO:10).

Kits

The present disclosure also provides diagnostic kits for carrying out the methods disclosed herein. In one example, the diagnostic kit includes the RNA aptamer or the diagnostic agent as described herein for detecting CD133 expressing cells (e.g. cancer stem cells).

The kit may also include ancillary agents such as buffering agents and stabilising agents. The diagnostic kit may further include agents for reducing background interference, control reagents and an apparatus for conducting a test. Instructions on how to use the diagnostic kit are generally also included.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

EXAMPLES

Methods
Cell Lines and Cell Culture.

The cell lines of human origin used in this study were purchased from American type Culture Collection. They are human colorectal cancer HT-29; human hepatocellular carcinoma Hep3B; human glioblastoma multiforme carcinoma T98G; and human embryonic kidney cells HEK293T. Cells were grown and maintained in culture with Dulbecco's Modified Eagle medium (DMEM) (Invitrogen, Victoria, Australia) supplemented with 10% fetal calf serum (HEK293T, HT-29), or Minimum Essential Medium (MEM) (Invitrogen) supplemented with 10% fetal calf serum (Hep3B, T98G). Cells were maintained at 37° C. in a 5% $CO_2$ atmosphere.

Protein Expression and Cell SELEX.

Human CD133 cDNA was purchased from Invitrogen and cloned into a mammalian expression vector, pcDNA 3.1/V5-His-TOPO. The recombinant 6× Histine-tagged CD133 was transiently expressed in HEK293T cells. Briefly, HEK293T cells were seeded in 100 mm or 60 mm dishes to reach 70% confluency after 24 hour incubation, and transfected with a total of 24 or 8 ug, respectively, of CD133 using Lipofectamine 2000 (Invitrogen Life Technologies) in antibiotic-free medium according to the manufacturer's instructions. Following a 72 hour incubation, the transfected cells were used as the target for cell SELEX.

SELEX Selection.

A DNA library containing a central 40-nt randomised sequence (5'-<u>TAA TACGACTCACTATAG</u> GGA GAC AAG AAT AAA CGC TCA A-N40-TTC GAC AGG AGG CTC ACA ACA GGC (SEQ ID NO:11), with the T7 RNA polymerase promoter sequence underlined) was synthesised (GeneWorks, Australia). The double stranded DNA pool was generated from the original synthetic library via a large scale PCR using primers flanking the randomised sequence, 5'-TAA TAC GAC TCA CTA TAG GGA GAC AAG AAT AAA CGC TCA A-3' (SEQ ID NO:12) and 5'-GCC TGT TGT GAG CCT CCT GTC GAA-3' (SEQ ID NO:13). A portion of the large-scale PCR products (~$10^{14}$ sequences) was used as a template for in vitro transcription to produce the initial 2'-fluoropyrimidine modified RNA pool using a Durascribe® T7 Transcription kit (EPICENTRE® Biotechnologies, USA). For SELEX, RNA, at a concentration of 5 µM for initial selection or 1 µM for each iterative rounds, was diluted in 100 µL of binding buffer (Dulbecco's phosphate buffered saline containing 2.5 mM $MgCl_2$, 0.1 mg/mL tRNA and 0.1 mg/mL Salmon sperm) and denatured at 85° C. for 5 minutes, allowed to cool to room temperature for 10 min, and annealed at 37° C. for 15 min, before incubating with the target protein expressed in HEK293T cells for 1 h at 4° C. Following incubation and extensive washes, the bound RNA was reverse transcribed using SuperScript III Reverse Transcriptase (Invitrogen), followed by PCR amplification and in vitro transcription and used for the next round of SELEX. Counter-selection steps were included from round 4, using a His-tagged irrelevant protein expressed in HEK293T cells, to decrease the enrichment of species specifically recognising the His-tag, the HEK293T cells or the tissue culture plate. The number of PCR amplification cycles was also optimised to prevent over-amplification of non-specific "parasite" PCR products. In addition, the stringency of the selection process was enhanced to promote the selection of high-affinity aptamers through adjustments to aptamer concentration, incubation times, and the number of washes. To acquire aptamers of high specificity, the number of cells used was progressively decreased while the washing stringency increased during the progression of SELEX, with negative selections included from round four. Enrichment was monitored using restriction fragment length polymorphism (RFLP) and flow cytometry using live cells.

RFLP Analysis.

The enrichment of aptamer candidates during selection was determined by Restriction fragment length polymorphism (RFLP). Briefly, RFLP was performed as previously described (Das et al. 2009; Missailidis & Hardy 2009), with minor modifications. Approximately 5 ng of cDNA from iterative cycles was amplified by PCR for eight cycles. The amplified DNA was digested with 4 restriction enzymes, Afa I, Alu I, Hha I and Xsp I that recognise 4 nucleotides (frequent cutters) in Buffer T supplied by the manufacturer (Takara) with 0.1% (w/v) bovine serum albumin at 37° C. overnight. Following the overnight digestion, the DNA was heated to 65° C., cooled on ice, and separated via electrophoresis on a native 20% polyacrylamide gel in TBE buffer. The gel was then stained in GelStar and visualized using a standard gel imaging system.

Flow Cytometry Assays.

Cells were harvested at 80% confluence with trypsin digestion and resuspended in washing buffer (DPBS with 2.5 mM $MgCl_2$) and enumerated. Following centrifugation (1000×g for 5 min), the cell pellet was resuspended in binding buffer (DPBS supplemented with 5 mM $MgCl_2$, 0.1 mg/ml tRNA, 0.1 mg/ml salmon sperm DNA) and diluted to $1\times10^6$/mL.

To confirm aptamer binding to the target protein, RNA from iterative rounds were labelled at the 3'-ends with fluorescein isothiocyanate (FITC) according to a previously described method (Willkomm & Hartmann (2005). Weinheim, Wiley-VCH GmbH & Co. KGaA 1:86-94). Amber tubes were used throughout to minimise photo-bleaching. Briefly, samples were oxidized with sodium periodate. The oxidation was terminated with the addition of 10 mM ethylene glycol, followed by ethanol precipitation. FITC was added at a 30-molar excess, and the reaction was completed overnight at 4° C. One µM of FITC-labelled RNA was incubated with trypsinised $5\times10^5$ HEK293T transfected with CD133 protein or non-transfected HEK293T cells in 100 µL of binding buffer for 1 h on ice, followed by washing three times and resuspension in 300 µL of binding buffer. Fluorescent intensity was determined with a FACS Canto II flow cytometer (Becton Dickinson) by counting 50,000 events each sample. The FITC-labelled RNA from the unselected library was used to determine non-specific binding.

The binding for each round was calculated after subtracting the mean fluorescence intensity of the binding of round zero RNA to target cells as well as that for binding to negative control cells according to a method described by Ellington and colleagues (Li et al. (2009). J. Proteome Res 8:2438-48).

Cloning, Sequencing and Structural Analysis of Selected Aptamers.

Following RFLP and flow cytometric analyses of iterative rounds, round six demonstrated sufficient enrichment of RNA sequences that selectively recognised the target protein. This enriched pool was amplified by PCR for ten cycles and the PCR products were cloned into the plasmid pCR® 4-TOPO® (Invitrogen). Plasmid DNA from individual clones were prepared and their sequence determined using an automated DNA sequencing procedure. The aptamer sequences were analysed using ClustalX2 (Larkin et al. (2007) Bioinformatics 23:2947-8). Secondary structures were predicted using the program RNAfold (Hofacker (2003) Nucleic Acids Res 31:3429-31).

Determination of Aptamer Affinity.

The dissociation constant ($K_d$) of successful 2'-fluoropyrimidine RNA aptamer species to native CD133 expressed on the cell surface was determined using flow cytometry. HEK293T cells transfected with CD133 protein, or non-transfected HEK293T cells ($5\times10^5$) were first incubated with blocking buffer (binding buffer containing 0.2% (w/v) sodium azide) followed by two washes with binding buffer prior to incubation with serial concentrations (approximately 10-fold above and below the apparent $K_d$) of FITC-labelled aptamer in a 100 µL volume of binding buffer for 1 h on ice. The cells were washed three times with binding buffer, resuspended in 150 µL binding buffer and subjected to flow cytometric analyses. The FITC-labelled unselected library was used as a negative control. The mean fluorescence intensity (MFI) of the unselected library was subtracted from that of the aptamer-target cell to generate the MFI of specific binding. The $K_d$ for each aptamer was determined by Scatchard analysis according to the equation:

$$[\text{Bound aptamer}]/[\text{aptamer}] = -(1/K_d)\times[\text{bound aptamer}]+([T]_{tot}/K_d)$$

where $[T]_{tot}$ represents the total target concentration.

Aptamer Truncation and Determination of Specificity.

To generate the truncated aptamers, the sense and antisense DNA oligonucleotides of desired sequences were synthesised. CD133-1-1 ($1^{st}$ Truncation) was derived from a sense oligonucleotide, 5'-<u>TAA TACGACTCACTATAG</u> AGA CAA GAA TAA ACG CTC AAC CCA CCC TCC TAC ATA GGG AGG AAC GAG TTA CTA TAG-3' (SEQ ID NO:14), and antisense oligonucleotide, 5'-CTA TAG TAA CTC GTT CCT CCC TAT GTA GGA GGG TGG GTT GAG CGT TTA TTC TTG TCT C-3' (SEQ ID NO:15); CD133-1-2 ($2^{nd}$ truncation) was derived from a sense oligonucleotide: 5'-<u>TAA TACGACTCACTATAG</u> CTC AAC CCA CCC TCC TAC ATA GGG AGG AAC GAG T-3' (SEQ ID NO:16) and an antisense oligonucleotide, 5'-ACT CGT TCC TCC CTA TGT AGG AGG GTG GGT TGA GC-3' (SEQ ID NO:17); CD133-1-2-1 ($3^{rd}$ Truncation) was derived from a sense oligonucleotide, 5'-<u>TAA TACGACTCACTATAC</u> CAC CCT CCT ACA TAG GGT GG-3' (SEQ ID NO:18) and an antisense oligonucleotide, 5'-CCA CCC TAT GTA GGA GGG TGG-3' (SEQ ID NO:19); and CD133-1-2-2 ($4^{th}$ Truncation) was derived from a sense oligonucleotide, <u>TAA TACGACTCACTATAC</u> CCT CCT ACA TAG GG-3' (SEQ ID NO:20) and an antisense oligonucleotide, 5'-CCC TAT GTA GGA GGG-3' (SEQ ID NO:21). CD133-2-1 ($1^{st}$ Truncation) was derived from a sense oligonucleotide 5'-<u>TAA TACGACTCACTATAC</u> AGA ACG TAT ACT ATT CTG-3' (SEQ ID NO:22) and an antisense oligonucleotide, 5'-CAG AAT AGT ATA CGT TCT G-3' (SEQ ID NO:23) (T7 RNA promoter sequence is underlined). The relevant pairs of oligonucleotides were mixed in equal molar ratios in 1×PEI buffer (0.1 M Tris-HCl pH 8, 0.1 M $MgCl_2$ 0.5 M NaCl and 0.1 M dithiothreitol), heated for 5 min at 90° C. and cooled slowly to room temperature prior to ethanol precipitation. In vitro transcription and FITC-labelling was performed as described above. The final truncations of these clones (CD133-1-4 and CD133-2-1), 5'-DY647-CCC TCC TAC ATA GGGdT-3' (SEQ ID NO:24) and 5'-DY647-CAG AAC GTA TAC TAT TCT GdT-3' (SEQ ID NO:25), were also chemically synthesized with a 5'-DY647 fluorescent tag and a 3'-inverted deoxythymidine (Dharmacon). The binding affinities of these two aptamers and a negative control aptamer was determined using CD133 positive (HT-29 and Hep3B) and CD133 negative cell lines (T98G and HEK293T). The blocking step was performed at 4° C. using blocking buffer containing 5% (v/v) fetal calf serum, whilst the binding of the aptamers was performed at 37° C. for 30 min.

Confocal Microscopy.

Twenty-four hours prior to labelling, cells were seeded at a density of 75,000 cells per cm$^2$ in an glass-bottom 8-chamber slide (Lab-Tek II, Nunc). DY647-CD133-1-2-2, DY647-CD133-2-1 and the control aptamer were prepared in the same manner as for flow cytometry. Following removal of media, cells were incubated in blocking buffer containing 5% (v/v) serum at 37° C. for 15 min, washed twice in binding buffer prior to incubation with 200 nM aptamer for 30 min at 37° C. Bisbenzimide Hoechst 33342 (3 µg/mL) (Sigma) was added to the cells during the final 15 mins of incubation. The aptamer solution was removed and the cells washed 3 times for 5 min each in binding buffer prior to visualisation using a FluoView FV10i laser scanning confocal microscope (Olympus).

Inhibition of Endocytosis.

This was performed essentially as described for confocal microscopy with minor modifications.

Briefly, cells were pre-treated with either a potassium-depleted (50 mM Hepes, 140 mM NaCl, 2.5 mM MgCl$_2$, and 1 mM CaCl$_2$) or a hypertonic buffer (potassium-depleted buffer containing 3 mM KCl and 450 mM sucrose) for 1 hr at 37° C. These buffers were also used in the incubation step with aptamers and all rinsing steps. The effectiveness of these treatments in inhibiting endocytosis was verified by qualitatively characterising the internalisation of human transferrin conjugated to Alexa Fluor 488 (Invitrogen). Transferrin (5 µg/mL) was added to the cells following pre-treatment followed by a 30 min incubation at 37° C. The cells were washed three times in their respective buffers and visualised using the FluoView FV10i confocal microscope.

Colocalisation of Aptamers with Transferrin.

HT-29, Hep3B, T98G and 293T cells were prepared as previously described for confocal microscopy. Following removal of media, cells were incubated in blocking buffer containing 5% (v/v) serum at 37° C. for 15 min, washed twice in binding buffer prior to incubation with 200 nM aptamer for 30 min at 37° C. The aptamer solution was removed and the cells washed 3 times for 5 min each in binding buffer. Transferrin were then added to the cells and incubated for 2 hours prior to Bisbenzimide Hoechst 33342 (3 µg/mL) (Sigma) being added to the cells during the final 15 mins of incubation. The cells washed 3 times for 5 min each in binding buffer prior to visualisation using a FluoView FV10i laser scanning confocal microscope.

Tumour Sphere Preparation and Incubation with Aptamers and Antibody.

One to two thousand HT29 and HEK293T cells were plated out and allowed to form spheres for 7 days in DMEM/F12 media (Invitrogen Life Technologies) containing epidermal growth factor, basic fibroblast growth factor, insulin and B27. At 7 days, the spheres (of the size of 300~400 µm) were washed three times in PBS containing 2.5 mM MgCl$_2$ and blocked for 20 minutes using binding buffer. The spheres were then incubated with 100 nM of aptamer or AC133 antibody for, 30 min, 60 min, 120 min, 240 min or 24 hours. Following each time point, the spheres were washed three times with PBS prior to visualisation using the FluoView FV10i confocal microscope.

Example 1: Cell SELEX Facilitates the Selection of Aptamers Against Complex Protein Targets CD133 is a complex pentaspan protein containing two extracellular loops. To effectively select aptamers against only the extracellular portion of the protein, it was necessary to devise a procedure that allowed the inventors to express CD133 in its native conformational form. To this end, the inventors sought to transiently express the protein on the surface of HEK293T cells. Using Lipofectamine 2000, CD133 was transfected into HEK293T cells and allowed to express for 72 hours prior to SELEX experiments, with expression confirmed by AC133 antibody staining. Similar to previous SELEX experiments, a random RNA library of approximately $1 \times 10^{14}$ species containing 2'fluoro-modified ribose on all pyrimidines was incubated with expressed CD133 on the surface of HEK293T cells. Unbound RNA was removed via several washing steps prior to RT-PCR, and the process was repeated for a total of 12 rounds. Non-specific binding was eradicated through negative selection using an irrelevant His-tagged protein transfected into HEK293T cells. Non-radioactive RFLP was performed to confirm evolution of the species during iterative rounds and confirmation of enrichment was determined using flow cytometry using transfected and non-transfected HEK293T cells. As shown in FIG. 1, round six showed a greater than 2.5 fold increase in binding, to CD133-transfected HEK293T cells, as compared to non-transfected HEK293T cells and that of the unselected library.

Example 2: Post-SELEX Engineering Generated the Smallest Tumour-Specific Aptamer Round six was cloned and sequenced and the clones were fluorescently tagged with FITC using an in-house method. The binding specificity of each clone was determined using transfected and non-transfected HEK293T cells and the most encouraging results were shown with two aptamers, designated CD133-1 and CD133-2. These two clones were sequentially truncated to determine the shortest number of bases required to maintain the structure of the binding region of the aptamer, as well as reducing the $K_d$ and therefore, increasing the binding affinity (Table 1).

TABLE 1

Sequences of CD133 aptamers and their truncations.

| | Sequence | Length (number of nucleotides) |
|---|---|---|
| CD133-1 | GAG ACA AGA AUA AAC GCU CAA CCC ACC CUC CUA CAU AGG GAG GAA CGA GUU ACU AUA GAG CUU CGA CAG GAG GCU CAC AAC | 81 |

TABLE 1-continued

Sequences of CD133 aptamers and their truncations.

| | Sequence | Length (number of nucleotides) |
|---|---|---|
| CD133-1-1 | GAG ACA AGA AUA AAC GCU CAA CCC ACC CTC CUA CAU AGG GAG GAA CGA GUU ACU AUA G | 58 |
| CD133-1-2 | GCU CAA CCC ACC CUC CUA CAU AGG GAG GAA CGA GU | 35 |
| CD133-1-2-1 | CC ACC CUC CUA CAU AGG GUG G | 21 |
| CD133-1-2-2 | CC CUC CUA CAU AGG G | 15 |
| CD133-2 | GAGACAAGAAUAAACGCUCAAGGAAAGCGCUUAUUGUUU GCUAUGUUAGAACGUAUACUAUUUCGACAGGAGGCUCAC AACAGGC | 85 |
| CD133-2-1 | CAGAACGUAUACUAUUCUG | 19 |

Clone CD133-1 was truncated a total of four times to confirm the binding region of the aptamer. This clone was successfully truncated to 15 nucleotides, making it the smallest published aptamer against a tumour-specific antigen, and equivalent in size to the smallest published DNA aptamer directed against thrombin (Paborsky et al. (1993) J. Biol Chem 268:20808-11). A second clone, CD133-2, was also investigated for its potential to bind with high affinity and specificity to CD133. Truncating the aptamer resulted in a reduced $K_d$, and therefore a higher affinity for the target (Table 2).

TABLE 2

CD133 dissociation binding constants against CD 133-positive (HT-29 & Hep3B) and CD133-negative (T98G & HEK293T) cells

| Cell Line | CD133-1-2-2 (Kd, nM) | CD133-2-1 (Kd, nM) |
|---|---|---|
| HT-29 | 82 | 145 |
| Hep3B | 32 | 52 |
| HEK293T | 1.20E+05 | 1.74E+06 |
| T98G | 2.75E+05 | 4763 |

Confirmation of the sensitivity and specificity of these two aptamers was determined using both CD133-positive (HT-29 and Hep3B) and CD133-negative (T98G and HEK293T) cell lines (Table 2). The $K_d$ was increased slightly when the species were commercially synthesized and labelled with a DyLight fluorophores.

Example 3: CD133-Specific Aptamers are Internalised Via Receptor-Mediated Endocytosis As we have previously reported, for an aptamer to be classed as an effective cancer theragnostic, it must be efficiently internalised following binding to its target. Following incubation with both CD133 positive and CD133 negative cells at 37° C. for 30 minutes, internalisation was quantified using confocal microscopy (FIG. 5). Internalisation was considered specific due to the lack of fluorescent signal seen with CD133-negative cell lines. Internalisation via receptor-mediated endocytosis was confirmed via endocytic blockade, such as potassium-depletion and hypertonic treatments. The effectiveness of these treatments has been previously confirmed using transferrin (Shigdar et al. (2011a) Cancer Sci 102:991-8) and as shown in FIG. 6.

Example 4: CD133-Specific Aptamers Show Superior Penetration of Tumor Spheres than CD133 Antibodies In an attempt to demonstrate the effectiveness of our aptamers as cancer theranostics, the inventors investigated the potential of their aptamers to penetrate a tumour mass using an in vitro tumour sphere as a model for in vivo targeting. The inventors generated tumour sphere models of HT-29 (CD133$^+$) and HEK293T (CD133$^-$) cell lines and incubated these spheroids with CD133-1, CD133-2 and an AC133 antibody for 4 h followed by confocal microscopy (FIG. 7).

Example 5: CD133 Aptamer-Doxorubicin Conjugate is Able to Eliminate Colon Cancer Stem Cells In Vitro With a few exceptions, chemotherapy drugs, such as doxorubicin, do not kill cancer stem cells. The inventors hypothesized the if chemotherapy drugs are delivered to cancer stem cells by CD133 aptamer and enter the cells via endocytosis instead of random diffusion into the cells as free drugs, they could transform the conventional chemotherapy drugs into an effective cancer stem cell killer. To test the ability of CD133 aptamer-doxorubicin in elimination of colon cancer stem cell in vitro, the inventors conducted an in vitro tumoursphere assay.

The CD133-2-1 aptamer was conjugated to doxorubicin. Three different cell doses of colon cancer cells (HT29) were seeded in 96 ultra-low attachment plates with cancer stem cell medium (serum-free DMEM medium supplemented with insulin, FGF, EGF, and B27) that promote tumoursphere formation. Cells were treated with saline (PBS) control, 1 µM of DOX-Aptamer conjugate, or 1 µM of free doxorubicin. The tumoursphere formation in each well was evaluated 3 days post-treatment (Table 3).

At a cell dose of 100 cells/well, both CD133-2-1 Aptamer-Dox conjugate and free doxorubicin showed no effect on inhibition of tumoursphere formation. However, at a cell dose of 50 cells per well, a slight decrease in frequency was observed with the Aptamer-Dox. Importantly, under the 10 cells/well condition, treatment of 1 µM of DOX-Aptamer conjugate led to complete elimination of colon cancer stem-like cells capable of forming tumourspheres. Therefore, cancer stem cell-targeted delivery of doxorubicin via CD133 aptamer can bypass the known chemoresistance mechanisms underlying cancer stem cell's ability of resistance to conventional anti-cancer therapy.

TABLE 3

Tumoursphere formation after treatment

|  | Control (PBS) | Doxorubicin (Dox) | Aptamer-Doxorubicin conjugate |
|---|---|---|---|
| 100 cells/well | 5/5 | 5/5 | 5/5 |
| 50 cells/well | 5/5 | 5/5 | 3/5 |
| 10 cells/well | 4/5 | 5/5 | 0/5 |

Remarks

Cancer stem cells (CSCs) are considered to be the root of cancer and the cause of cancer recurrence. This model has gained acceptance because it explains radiation- and chemotherapy-resistance (Visvader & Lindeman (2012) Cell Stem Cell 10:717-28), and has led to numerous attempts to specifically target this population of cells within the tumour. While there is not one specific marker which defines all CSCs, a number of markers, including CD133, CD44, ALDH, EpCAM and ABCG2 (Hu & Fu (2012) Cancer Res 2:340-56; Visvader & Lindeman 2012 supra), have proven useful for defining the CSC population in solid tumours. CD133 has been implicated as a marker of the CSC population in brain, prostate, pancreas, melanoma, colon, liver, lung and ovarian cancers. While the function of CD133 is still to be elucidated, this marker is upregulated in hypoxic conditions and has been associated with vasculogenic mimicry in triple negative breast cancer and prostate cancer (Liu et al. (2012a) Cancer Biol Ther May 1 13(7); Liu et al. (2012b) Oncogene Apr 2), indicating the importance of CD133 in tumour growth and metastasis. Given how critical these CD133+ cells could be to the generation, maintenance and continuing spread of the tumour, we have isolated RNA aptamers against CD133.

The inventors have previously described the success of the SELEX procedure to isolate aptamers targeting another CSC marker (Shigdar et al. 2011 a supra). The isolation of aptamers targeting CD133 required a modification to previous protocols due to the pentaspan nature of this protein and the necessity to use proteins in their conformational shape for selection of aptamers. The success of the selection protocol was shown using flow cytometric binding assays, as well as RFLP analysis. Successful evolution was shown following the sixth SELEX cycle, and several aptamers were cloned. Two aptamers were chosen for further characterisation using both CD133-positive and -negative cell lines. These aptamers were also truncated to determine the minimal size required to maintain binding affinity. One of these aptamers, CD133-1 was able to be truncated to a size of 15 bases. This truncation makes this the smallest RNA aptamer described and equal in size to the DNA aptamer targeting thrombin (Paborsky et al. 1993 supra). Both of these aptamers were shown to be sensitive and specific, and more importantly, these two aptamers were rapidly internalised by receptor-mediated endocytosis following binding to their target. This latter feature of the aptamers is a necessary requirement for these aptamers to be modified as theragnostic reagents.

Aptamers possess many benefits that make them ideal escort modalities for both treatment and imaging of tumour masses. Their small size means that they are capable of penetrating the tumour much more efficiently than conventional immunotherapy options, and these nucleic acids also lack immunogenicity, leading to far fewer side effects. Through the additional of functionalisation, either directly conjugating or encapsulating drugs in nanoparticles, aptamers can function as very effective drug escorts. There have been several reports of directly conjugating chemotherapeutic drugs, such as doxorubicin, siRNA or ribozyme to targeting aptamers, and the successful functionalisation of nanoparticles through the attachment of aptamers to their surface. While some aptamers can be effective solely by binding to their target, the majority of aptamers are much more successful as guiding hands to cytotoxic substances.

The claims defining the invention are as follows:

1. An RNA aptamer which specifically binds to CD133, comprising:
   (i) the sequence 5'-CCCUCCUACAUAGGG-3' (SEQ ID NO:1),
   (ii) a sequence of 15 contiguous nucleotides that is identical to SEQ ID NO: 1 except that it may contain two or four substitutions within the regions defined by nucleotides 1-4 and 12-15 of SEQ ID NO: 1 such that residues 1-4 and 12-15 remain complementary to each other and can form a duplex stem, while residues 5-11 form a loop structure capable of binding CD133,
   (iii) the sequence 5'-AGAACGUAUACUAUU-3' (SEQ ID NO: 7),
   (iv) the sequence 5'-CAGAACGUAUACUAUUCUG-3' (SEQ ID NO: 6), or
   (v) a sequence of 19 contiguous nucleotides that is identical to SEQ ID NO: 6 except that it may contain two, four, or six substitutions within the regions defined by nucleotides 1-5 and 15-19 of SEQ ID NO: 6 such that residues 1-5 and 15-19 remain complementary to each other and can form a duplex stem, while residues 6-14 form a loop structure capable of binding CD133.

2. The aptamer of claim 1 comprising a sequence selected from:

```
                                            (SEQ ID NO: 2)
(i) GAG ACA AGA AUA AAC GCU CAA CCC ACC CUC CUA

CAU AGG GAG GAA CGA GUU ACU AUA GAG CUU CGA CAG

GAG GCU CAC AAC;

(SEQ ID NO: 3)
(ii) GAG ACA AGA AUA AAC GCU CAA CCC ACC CUC CUA

CAU AGG GAG GAA CGA GUU ACU AUA G;

(SEQ ID NO: 4)
(iii) GCU CAA CCC ACC CUC CUA CAU AGG GAG GAA CGA

GU;

(SEQ ID NO: 5)
(iv) CC ACC CUC CUA CAU AGG GUG G;
and (SEQ ID NO: 1)
(v) CC CUC CUA CAU AGG G.
```

3. The aptamer of claim 1, wherein the aptamer comprises the sequence:
GAG ACA AGA AUA AAC GCU CAA GGA AAG CGC UUA UUG UUU GCU AUG UUA GAA CGU AUA CUA UUU CGA CAG GAG GCU CAC AAC AGG C (SEQ ID NO:8).

4. The aptamer of claim 1, consisting essentially of the sequence of SEQ ID NO:1 or SEQ ID NO:6.

5. The aptamer of claim 1, comprising one or more modifications that increase aptamer stability.

6. The aptamer of claim 5, wherein the aptamer comprises pyrimidine bases which are 2'-fluoro (2'F) modified.

7. The aptamer of claim 1, wherein the aptamer specifically binds to a $CD133^+$ cancer stem cell.

8. The aptamer of claim 7, wherein the cell is present in a biological sample obtained from a subject.

9. A diagnostic agent comprising the aptamer of claim 1 coupled to a detectable label selected from an enzyme, prosthetic group, fluorescent material, luminescent material, bioluminescent material, electron dense label, labels for MRI, radioactive material, and combinations thereof.

10. An anticancer agent comprising the aptamer of claim 1 coupled to a moiety selected from toxins, radionuclides, chemotherapeutic agents and combinations thereof.

11. A method of identifying a CD133 expressing cell and/or a cancer stem cell in a subject or in a biological sample, comprising contacting the cell with the aptamer of claim 1 or the diagnostic agent of claim 9.

12. A delivery agent comprising the aptamer of claim 1, coupled to an siRNA or ribozyme.

13. A composition comprising a therapeutically effective amount of:
   the aptamer of claim 1,
   the anticancer agent of claim 10, or
   the delivery agent of claim 12, and
   a pharmaceutically acceptable carrier and/or excipient.

14. A method of localizing a tumor in vivo, comprising administering the diagnostic agent of claim 9 to a subject.

15. The aptamer of claim 1, wherein the aptamer comprises a sequence comprising at least two substitutions within the sequence of SEQ ID NO:1.

16. The aptamer of claim 1, wherein the 3' end of the aptamer is modified to protect it from nuclease digestion.

17. The aptamer of claim 1 which has a dissociation constant for CD133 of about 150 nM or less.

18. A method for treating cancer in a subject comprising administering to the subject an anti-cancer agent comprising an RNA aptamer according to claim 1 coupled to an anticancer moiety.

19. The aptamer of claim 1, wherein the aptamer is modified by coupling the 5' end to a fluorophore, inverted dT, or PEG molecule.

* * * * *